United States Patent
Shelton, IV

(10) Patent No.: US 7,303,108 B2
(45) Date of Patent: **\*Dec. 4, 2007**

(54) SURGICAL STAPLING INSTRUMENT INCORPORATING A MULTI-STROKE FIRING MECHANISM WITH A FLEXIBLE RACK

(75) Inventor: Frederick E. Shelton, IV, Hillsboro, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/318,105

(22) Filed: Dec. 23, 2005

(65) Prior Publication Data

US 2006/0097026 A1    May 11, 2006

Related U.S. Application Data

(63) Continuation-in-part of application No. 11/052,632, filed on Feb. 7, 2005, now Pat. No. 7,083,075, which is a continuation-in-part of application No. 10/673,930, filed on Sep. 29, 2003, now Pat. No. 6,905,057.

(51) Int. Cl.
*A61B 17/36* (2006.01)
(52) U.S. Cl. .................. 227/179.1; 227/19; 227/178.1; 227/176.1; 227/180.1
(58) Field of Classification Search ............ 227/176.1, 227/178.1, 179.1, 180.1, 19
See application file for complete search history.

(56) References Cited

U.S. PATENT DOCUMENTS

| | | | |
|---|---|---|---|
| 448,194 A | 3/1891 | Balbin | |
| 804,229 A | 11/1905 | Hutchinson | |
| 1,944,166 A | 1/1934 | Stratman | |
| 2,883,984 A | 4/1959 | Candido, Jr. et al. | |
| 3,269,630 A | 8/1966 | Fleisher | |
| 3,661,187 A | 5/1972 | Caveney et al. | |
| 3,837,555 A | 9/1974 | Green | |
| 3,949,924 A | 4/1976 | Green | |
| 3,955,581 A | 5/1976 | Spasiano et al. | |
| 4,154,239 A | 5/1979 | Turley | |
| 4,276,878 A | 7/1981 | Storz | |
| 4,580,712 A | 4/1986 | Green | |
| 4,589,870 A | 5/1986 | Citrin et al. | |
| RE32,214 E | 7/1986 | Schramm | |
| 4,606,343 A | 8/1986 | Conta et al. | |
| 4,664,305 A | 5/1987 | Blake, III et al. | |

(Continued)

FOREIGN PATENT DOCUMENTS

EP    0 070 230 A1    7/1982

(Continued)

*Primary Examiner*—Brian D. Nash
(74) *Attorney, Agent, or Firm*—Frost Brown Todd, LLC

(57) ABSTRACT

A surgical stapling and severing instrument particularly suited to endoscopic procedures incorporates a handle that produces separate closing and firing motions to actuate an end effector. In particular, the handle produces multiple firing strokes in order to reduce the required amount of force required to fire (i.e., staple and sever) the end effector. A flexible rack transmits these firing strokes to a firing rod that reciprocates in an elongate shaft to actuate the end effector. The flexible rack advantageously stows into a pistol grip of the handle when retracted to minimize handle length.

20 Claims, 18 Drawing Sheets

U.S. PATENT DOCUMENTS

| | | |
|---|---|---|
| 4,671,278 A | 6/1987 | Chin |
| 4,869,415 A | 9/1989 | Fox |
| 4,976,686 A | 12/1990 | Ball et al. |
| 5,040,715 A | 8/1991 | Green et al. |
| 5,307,976 A | 5/1994 | Olson et al. |
| 5,314,424 A | 5/1994 | Nicholas |
| 5,376,095 A | 12/1994 | Ortiz |
| 5,413,267 A | 5/1995 | Solyntjes et al. |
| 5,465,895 A | 11/1995 | Knodel et al. |
| 5,467,911 A | 11/1995 | Tsuruta et al. |
| 5,509,596 A | 4/1996 | Green et al. |
| 5,562,239 A * | 10/1996 | Boiarski et al. ......... 227/175.2 |
| 5,573,541 A | 11/1996 | Green et al. |
| 5,579,978 A | 12/1996 | Green et al. |
| 5,605,272 A * | 2/1997 | Witt et al. ............... 227/175.2 |
| 5,697,543 A * | 12/1997 | Burdorff .................. 227/176.1 |
| 5,706,997 A | 1/1998 | Green et al. |
| 5,706,998 A | 1/1998 | Plyley et al. |
| 5,728,108 A | 3/1998 | Griffiths et al. |
| 5,730,740 A | 3/1998 | Wales et al. |
| 5,735,445 A | 4/1998 | Vidal et al. |
| 5,735,848 A * | 4/1998 | Yates et al. ................... 606/48 |
| 5,735,874 A | 4/1998 | Measamer et al. |
| 5,762,256 A | 6/1998 | Mastri et al. |
| 5,779,132 A * | 7/1998 | Knodel et al. ........... 227/176.1 |
| 5,782,396 A | 7/1998 | Mastri et al. |
| 5,810,811 A * | 9/1998 | Yates et al. ................... 606/50 |
| 5,855,311 A | 1/1999 | Hamblin et al. |
| 5,865,361 A | 2/1999 | Milliman et al. |
| 5,893,506 A | 4/1999 | Powell |
| 5,894,979 A | 4/1999 | Powell |
| 5,976,160 A | 11/1999 | Crainich |
| 6,004,335 A * | 12/1999 | Vaitekunas et al. ......... 606/169 |
| 6,032,849 A | 3/2000 | Mastri et al. |
| 6,079,606 A | 6/2000 | Milliman et al. |
| 6,120,526 A | 9/2000 | Daley |
| 6,241,139 B1 | 6/2001 | Milliman et al. |
| 6,330,965 B1 | 12/2001 | Milliman et al. |
| 6,656,193 B2 * | 12/2003 | Grant et al. ................. 606/151 |
| 6,755,338 B2 * | 6/2004 | Hahnen et al. .......... 227/175.1 |
| 6,786,382 B1 | 9/2004 | Hoffman |
| 6,830,174 B2 * | 12/2004 | Hillstead et al. ......... 227/175.1 |
| 6,905,057 B2 | 6/2005 | Swayze et al. |
| 6,964,363 B2 | 11/2005 | Wales et al. |
| 2002/0117533 A1 | 8/2002 | Milliman et al. |
| 2004/0232195 A1 | 11/2004 | Shelton et al. |
| 2004/0232196 A1 | 11/2004 | Shelton et al. |
| 2004/0232197 A1 | 11/2004 | Shelton et al. |
| 2004/0232199 A1 | 11/2004 | Shelton et al. |
| 2004/0232200 A1 | 11/2004 | Shelton et al. |
| 2005/0006430 A1 | 1/2005 | Wales et al. |
| 2005/0006431 A1 | 1/2005 | Shelton et al. |
| 2005/0006434 A1 | 1/2005 | Wales et al. |

FOREIGN PATENT DOCUMENTS

| | | |
|---|---|---|
| WO | WO 99/15086 | 4/1999 |

* cited by examiner

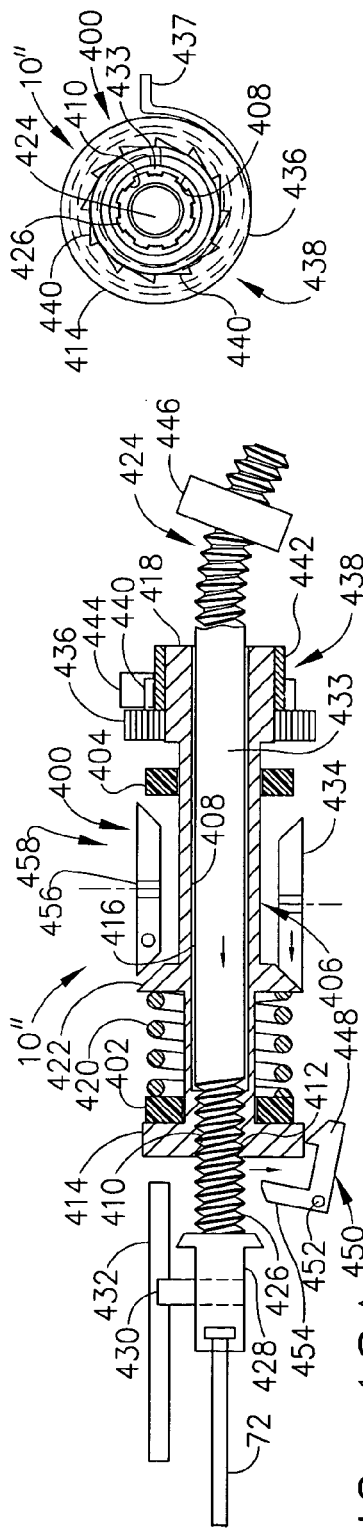
FIG. 18A
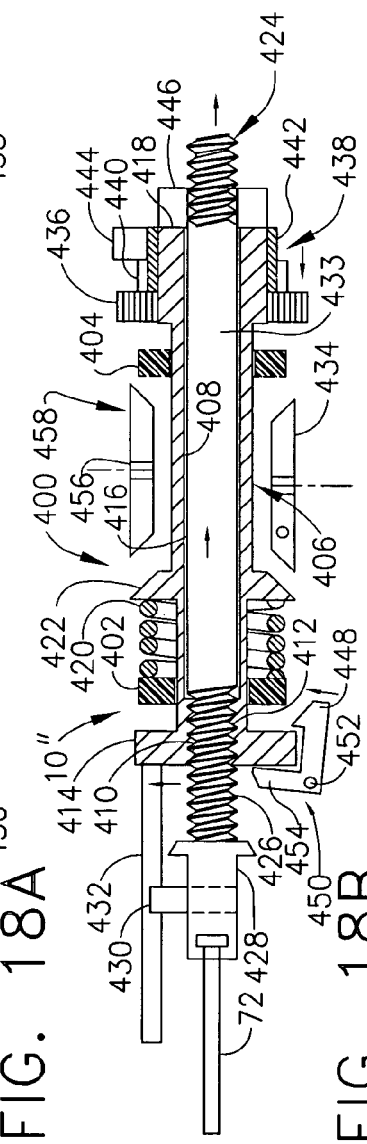
FIG. 18B
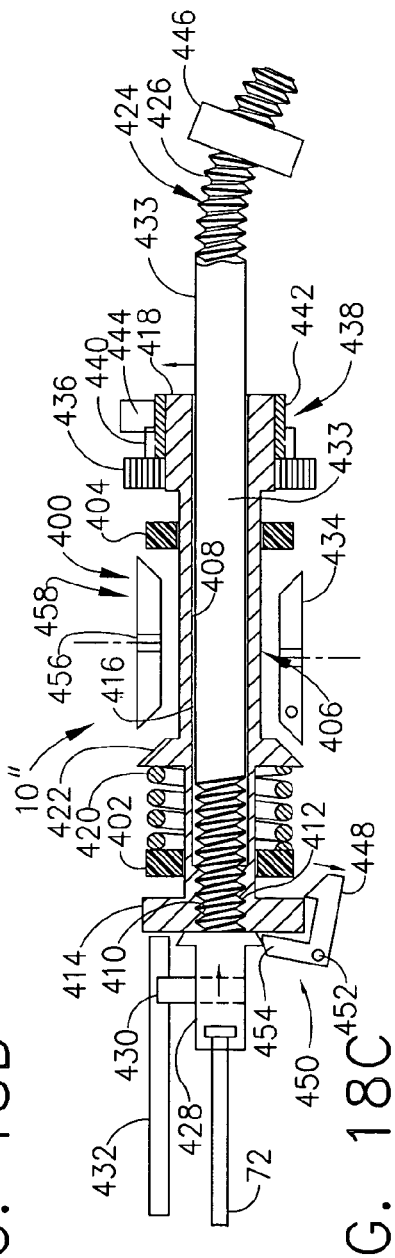
FIG. 18C
FIG. 18D

SURGICAL STAPLING INSTRUMENT INCORPORATING A MULTI-STROKE FIRING MECHANISM WITH A FLEXIBLE RACK

CROSS-REFERENCE TO RELATED APPLICATIONS

The present application is a continuation in part of U.S. patent application Ser. No. 11/052,632, "MULTI-STROKE MECHANISM WITH AUTOMATED END OF STROKE RETRACTION" to Jeffrey S. Swayze et al., filed Feb. 7, 2005, now U.S. Pat No. 7,083,075 which in turn was a continuation in part of U.S. patent application Ser. No. 10/673,930 filed Sep. 29, 2003 entitled "SURGICAL STAPLING INSTRUMENT INCORPORATING A FIRING MECHANISM HAVING A LINKED RACK TRANSMISSION", to Jeffrey S. Swayze, which issued as U.S. Pat. No. 6,905,057, the disclosures of both of which are hereby incorporated by reference in their entirety.

FIELD OF THE INVENTION

The present invention relates in general to surgical stapler instruments that are capable of applying lines of staples to tissue while cutting the tissue between those staple lines and, more particularly, to improvements relating to stapler instruments and improvements in processes for forming various components of such stapler instruments that accomplish firing with multiple strokes of a trigger.

BACKGROUND OF THE INVENTION

Endoscopic and laparoscopic surgical instruments are often preferred over traditional open surgical devices since a smaller incision tends to reduce the post-operative recovery time and complications. The use of laparoscopic and endoscopic surgical procedures has been relatively popular and has provided additional incentive to develop the procedures further. In laparoscopic procedures, surgery is performed in the interior of the abdomen through a small incision. Similarly, in endoscopic procedures, surgery is performed in any hollow viscus of the body through narrow endoscopic tubes inserted through small entrance wounds in the skin.

Laparoscopic and endoscopic procedures generally require that the surgical region be insufflated. Accordingly, any instrumentation inserted into the body must be sealed to ensure that gases do not enter or exit the body through the incision. Moreover, laparoscopic and endoscopic procedures often require the surgeon to act on organs, tissues and/or vessels far removed from the incision. Thus, instruments used in such procedures are typically long and narrow while being functionally controllable from a proximal end of the instrument.

Significant development has gone into a range of endoscopic surgical instruments that are suitable for precise placement of a distal end effector at a desired surgical site through a cannula of a trocar. These distal end effectors engage the tissue in a number of ways to achieve a diagnostic or therapeutic effect (e.g., endocutter, grasper, cutter, staplers, clip applier, access device, drug/gene therapy delivery device, and energy device using ultrasound, RF, laser, etc.).

Known surgical staplers include an end effector that simultaneously makes a longitudinal incision in tissue and applies lines of staples on opposing sides of the incision. The end effector includes a pair of cooperating jaw members that, if the instrument is intended for endoscopic or laparoscopic applications, are capable of passing through a cannula passageway. One of the jaw members receives a staple cartridge having at least two laterally spaced rows of staples. The other jaw member defines an anvil having staple-forming pockets aligned with the rows of staples in the cartridge. The instrument includes a plurality of reciprocating wedges which, when driven distally, pass through openings in the staple cartridge and engage drivers supporting the staples to effect the firing of the staples toward the anvil.

An example of a surgical stapler suitable for endoscopic applications is described in U.S. Pat. No. 5,465,895, which advantageously provides distinct closing and firing actions. Thereby, a clinician is able to close the jaw members upon tissue to position the tissue prior to firing. Once the clinician has determined that the jaw members are properly gripping tissue, the clinician can then fire the surgical stapler with a single firing stroke, thereby severing and stapling the tissue. The simultaneous severing and stapling avoids complications that may arise when performing such actions sequentially with different surgical tools that respectively only sever or staple.

Generally, a single closing stroke followed by a single firing stroke is a convenient and efficient way to perform severing and stapling. However, in some instances, it would be desirable for multiple firing strokes to be required. For example, surgeons are able to select from a range of jaw sizes with a corresponding length of staple cartridge for the desired length of cut. Longer staple cartridges require a longer firing stroke. Thus, to effect the firing, a hand-squeezed trigger is required to exert a larger force for these longer staple cartridges in order to sever more tissue and drive more staples, as compared to a shorter staple cartridge. It would be desirable for the amount of force to be lower, comparable to that needed for shorter cartridges so as not to exceed the hand strength of some surgeons. In addition, some surgeons not familiar with the larger staple cartridges may become concerned that binding or other malfunction has occurred when an unexpectedly higher force is required.

In U.S. Pat. No. 6,905,057, a multiple firing stroke handle for an endoscopic surgical stapling and severing instrument succeeds in reducing these firing forces by advancing a firing mechanism during each squeeze of the firing trigger, mechanically coupling this firing motion through a pawl into a linked rank. In addition to reducing the force required to squeeze the firing trigger, the linked rack stows into a pistol grip of the handle and advantageously reduces the length of the handle as compared to a rigid rack.

Consequently, a significant need exists for a surgical stapling instrument which has a multiple stroke firing mechanism with a reduced handle length.

BRIEF SUMMARY OF THE INVENTION

The invention overcomes the above-noted and other deficiencies of the prior art by providing a surgical stapling and severing instrument that advantageously incorporates a flexible firing member in a handle. The handle guides a distal portion of the flexible firing member longitudinally to translate a firing motion into a shaft firing member that translates in a shaft to actuate a distally attached end effector. The handle deflects a proximal portion of the flexible firing member from the longitudinal axis during retraction to advantageously reduce the required length of the handle.

These and other objects and advantages of the present invention shall be made apparent from the accompanying drawings and the description thereof.

BRIEF DESCRIPTION OF THE FIGURES

The accompanying drawings, which are incorporated in and constitute a part of this specification, illustrate embodiments of the invention, and, together with the general description of the invention given above, and the detailed description of the embodiments given below, serve to explain the principles of the present invention.

FIG. 18A is a left side view in elevation taken in vertical and longitudinal cross section through an alternative flexible threaded cable firing mechanism in an initial unfired state for the surgical stapling and severing instrument of FIG. 1.

FIG. 18B is a left side view in elevation taken in vertical and longitudinal cross section through the alternative flexible threaded cable firing mechanism of FIG. 18A in a fully fired state.

FIG. 18C is a left side view in elevation taken in vertical and longitudinal cross section through the alternative flexible threaded cable firing mechanism of FIG. 18B after automatic firing retraction.

FIG. 18D is a forward view in elevation taken in vertical and transverse cross section through the alternative flexible threaded cable firing mechanism of FIG. 18A.

DETAILED DESCRIPTION OF THE INVENTION

Figure 1:
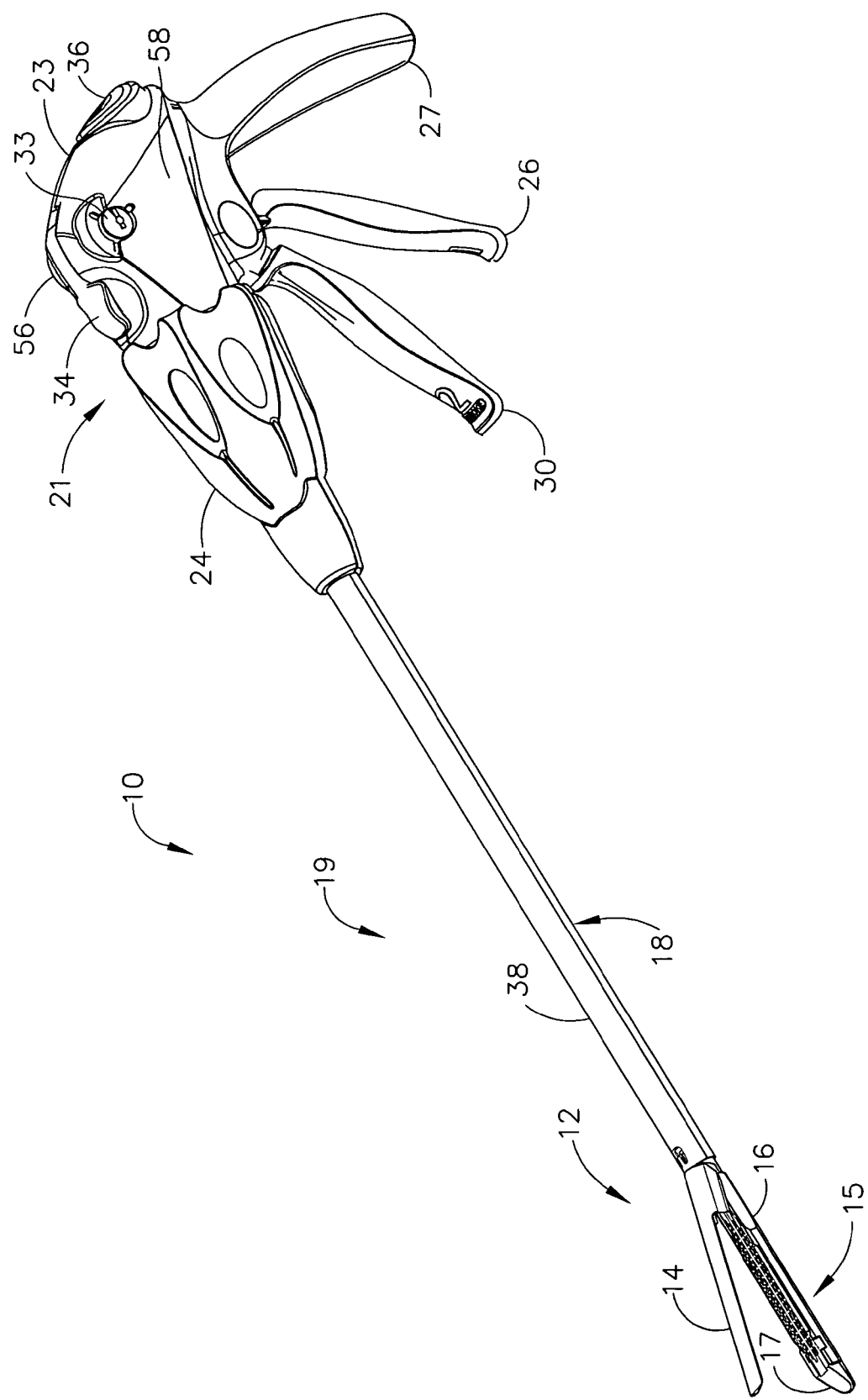
FIG. 1 is a left isometric view of a surgical stapling and severing instrument in an initial state with the closure and firing trigger released and the end effector (staple lying assembly) open.
Figure 2:
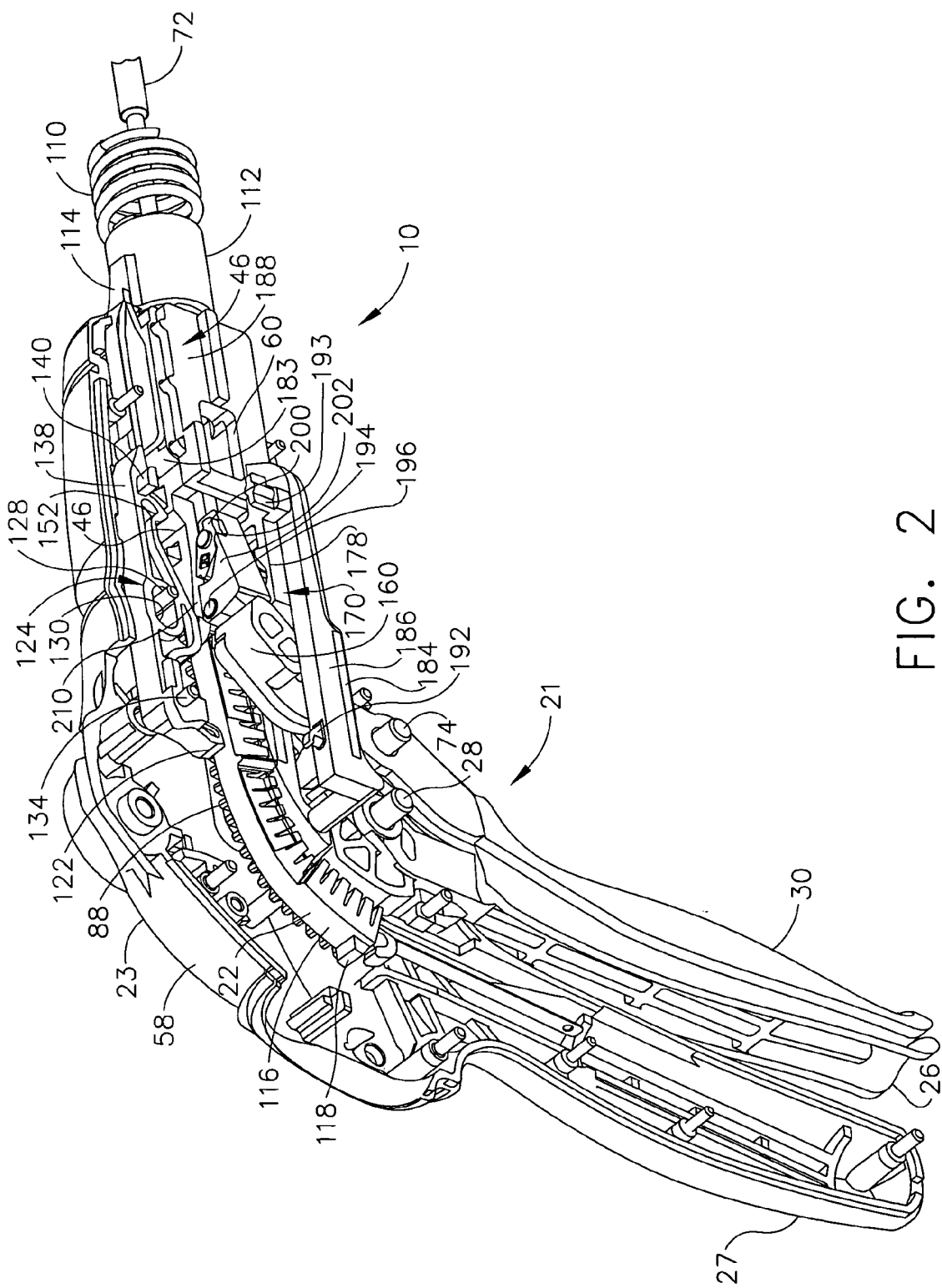
FIG. 2 is a right isometric exploded view of the surgical stapling and severing instrument of FIG. 1 with the staple applying assembly omitted.

In FIG. 1, a surgical stapling and severing instrument 10 includes multi-stroke firing of an end effector, which in the illustrative version is a staple applying apparatus 12. An upper jaw (anvil) 14 may be repeatably opened and closed about its pivotal attachment to a lower jaw 15 of an elongate (staple) channel 16 engaged to a replaceable staple cartridge 17. The staple applying assembly 12 is proximally attached to elongate shaft 18, forming an implement portion 19. When the staple applying assembly 12 is closed, the implement portion 19 presents a small cross-sectional area suitable for insertion through a trocar by an externally connected and manipulated handle 21. In FIG. 2, a flexible firing rack 22 incorporated into the handle 21 advantageously transfers firing motion to the implement portion 19 yet retracts to enable a reduced length handle 21.

Figure 3:
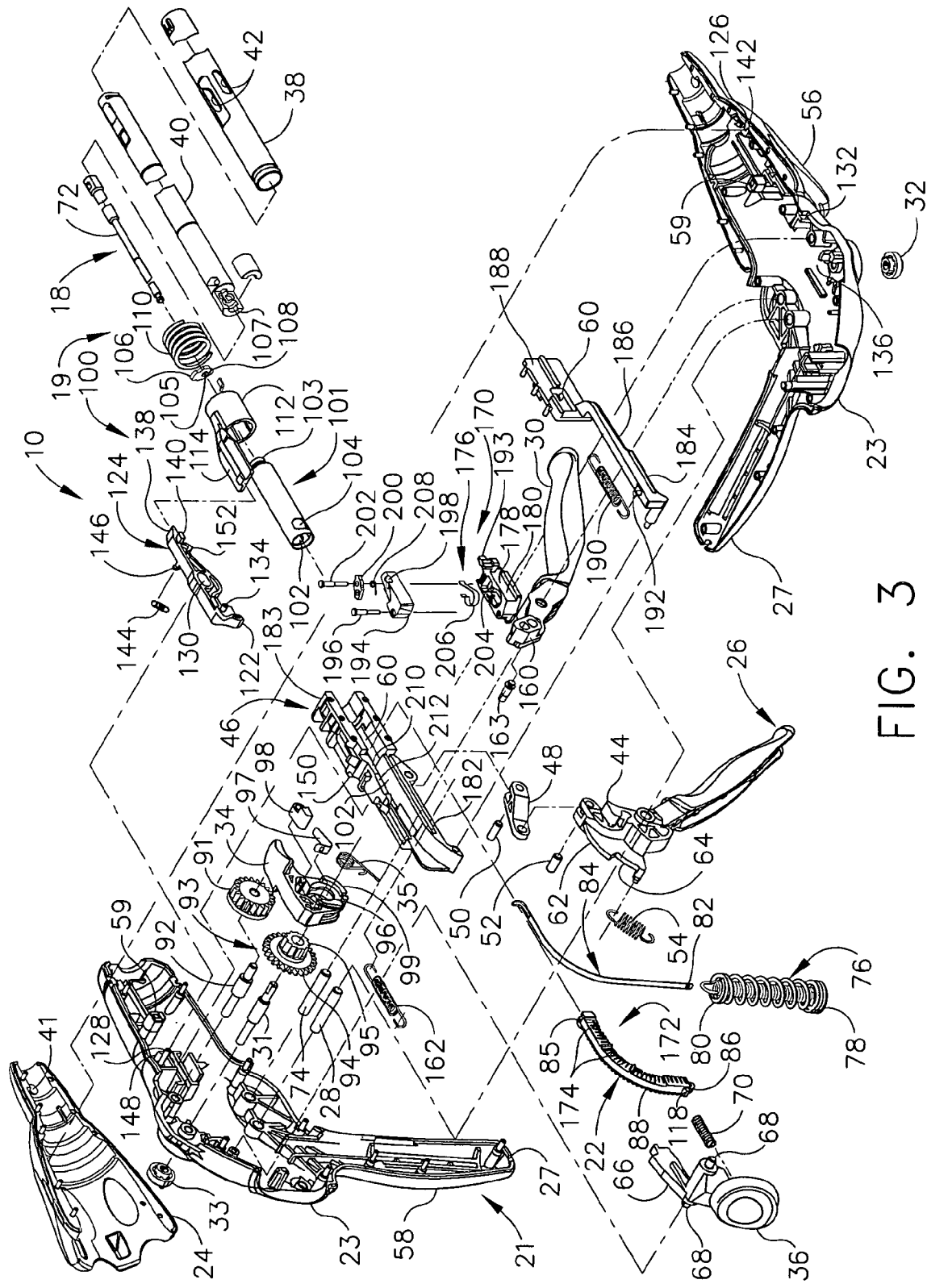
FIG. 3 is a right isometric view of a handle of the surgical stapling and severing instrument of FIG. 2 in a clamped and partially fired state with a right shell of a handle housing and rotation knob removed to expose a first version of a flexible firing rack consistent with aspects of the invention.

In FIGS. 1-3, the handle 21 has user controls mounted on its handle housing 23, such as a rotation knob 24 that rotates the elongate shaft 18 and staple applying assembly 12 about a longitudinal axis of the shaft 18. A closure trigger 26, which pivots in front of a pistol grip 27 about a closure trigger pin 28 engaged laterally across the handle housing 23, is depressed to close the staple applying assembly 12. A multiple stroke firing trigger 30, which pivots in front of the closure trigger 26, causes the staple applying assembly 12 to simultaneously sever and staple tissue clamped therein. Since multiple firing strokes are employed to reduce the amount of force required per stroke by the surgeon's hand, right and left indicator wheels 32, 33 (the former depicted in FIG. 3) that turn on an axle 31 (FIG. 3) rotate presenting indicia of the firing progress. For instance, full firing travel may require three full firing strokes and thus the indicator wheels 32, 33 rotate up to one-third of a revolution each per stroke. A manual firing release lever 34 allows retraction before full firing travel if desired and allows assistance to retract in the presence of binding or a failure in the retraction bias. The manual firing release lever 34 is normally downwardly biased by a coil spring 35 (FIG. 3). A closure release button 36 is outwardly presented when the closure trigger 26 is clamped and partial firing has not occurred that would prevent unclamping the closure trigger 26.

In FIG. 3, the elongate shaft 18 has as its outer structure a longitudinally reciprocating closure tube 38 that pivots the anvil 14 to effect closure in response to proximal depression of the closure trigger 26 of the handle 21. The elongate channel 18 is connected to the handle 21 by a frame 40 that is internal to the closure tube 38. The frame 40 is rotatably engaged to the handle 21 so that twisting the rotation knob 24 causes rotation of the implement portion 19. Each half shell of the rotation knob 24 includes an inward projection 41 that enters a respective longer side opening 42 in the closure tube 38 and projects inward to engage the frame 40 that determines the rotated position of the implement portion 19. The longitudinal length of the longer opening 42 is sufficiently long to allow longitudinal closure motion of the closure tube 38.

An upper portion 44 of the closure trigger 26 pushes forward a closure yoke assembly 46 via a closure link 48. The closure link 48 is pivotally attached at its distal end by a closure yoke pin 50 to the closure yoke assembly 46 and is pivotally attached at its proximal end by a closure link pin 52. The closure trigger 26 is urged to the open position by a closure trigger tension spring 54 that is connected proximally to the upper portion 44 of the closure trigger 26 and to the handle housing 23 formed by right and left half shells 56, 58. The right and left half shells 56, 58 each include a closure yoke guide post 59 that slides within respective horizontally elongate rectangular apertures 60 formed in each side of the closure yoke assembly 46, with the post 59 at a distal position in the respective aperture 60 when the closure yoke assembly 46 is proximally positioned with the anvil 14 open and at a proximal position in the aperture 60 when the closure yoke assembly 46 is distally positioned with the anvil 14 closed.

The upper portion 44 of the closure trigger 26 includes a proximal crest 62 with an aft notch 64. The closure release button 36 and a pivoting locking arm 66 are connected by a central lateral pivot 68. A compression spring 70 biases the closure release button 36 proximally (clockwise about the central lateral pivot 68 as viewed from the right). With the upper portion 44 back when the closure trigger 26 is released, the pivoting locking arm 66 rides upon the proximal crest 62 drawing in the closure release button 36. When the closure trigger 26 reaches its fully depressed position, it should be appreciated that the aft notch 64 is presented below the pivoting locking arm 66, which drops into and locks against the aft notch 64 under the urging of the compression spring 70. With the firing components retracted, manual depression of the closure release button 36 rotates the pivoting locking arm 66 upward, unclamping the closure trigger 26.

Once the closure trigger 26 is proximally clamped, a firing rod 72 is distally moved from the handle 21 in response to the multiple stroke firing trigger 30 being drawn to the pistol grip 27 with the amount of firing travel visible to the surgeon on right and left indicator gauge wheels 32, 33. The firing trigger 30 pivots about a firing trigger pin 74 that laterally traverses and is engaged to the right and left half shells 56, 58.

Figure 5:
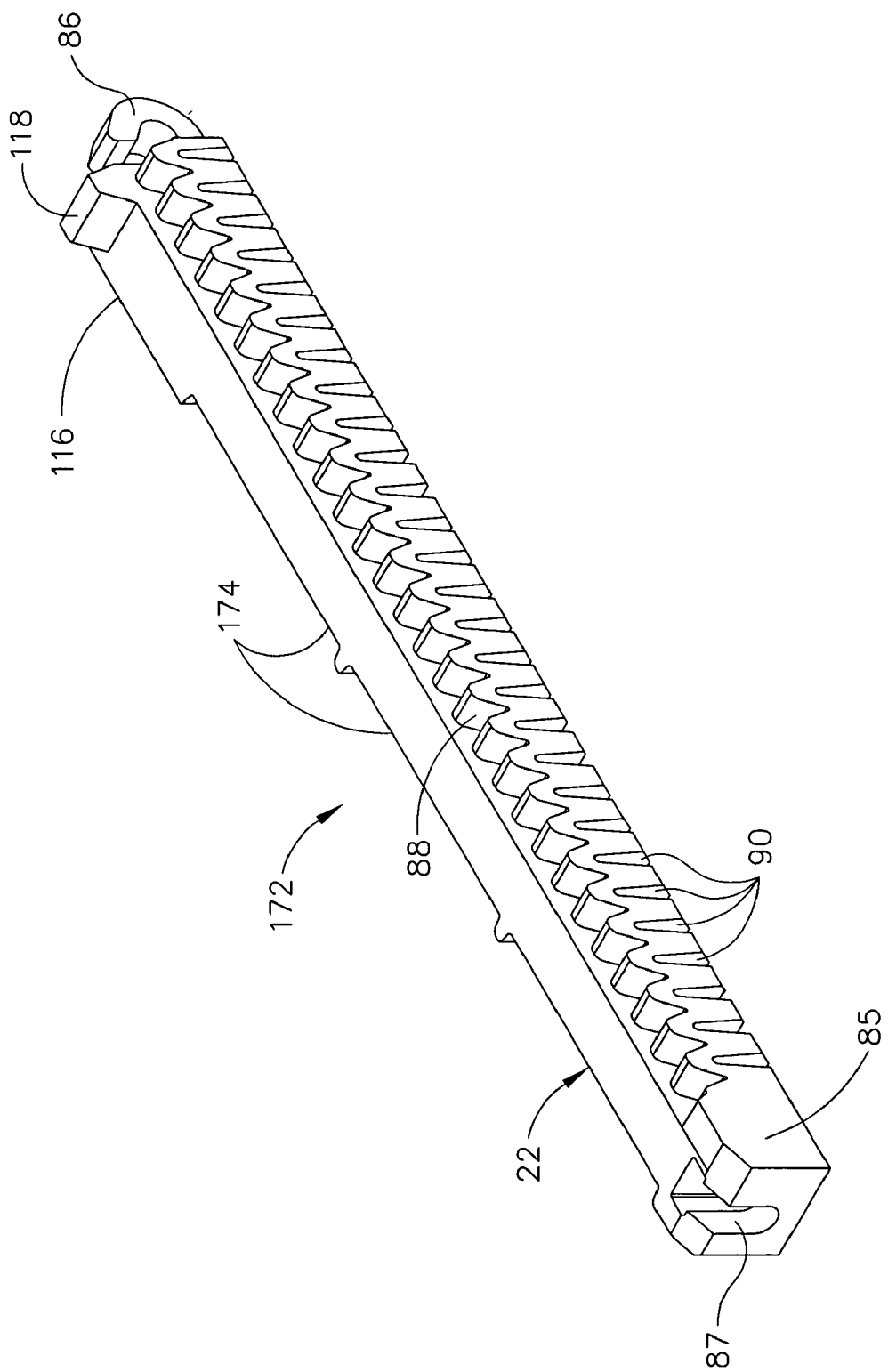
FIG. 5 is a front left isometric view of the flexible firing rack of FIG. 2.
Figure 6:
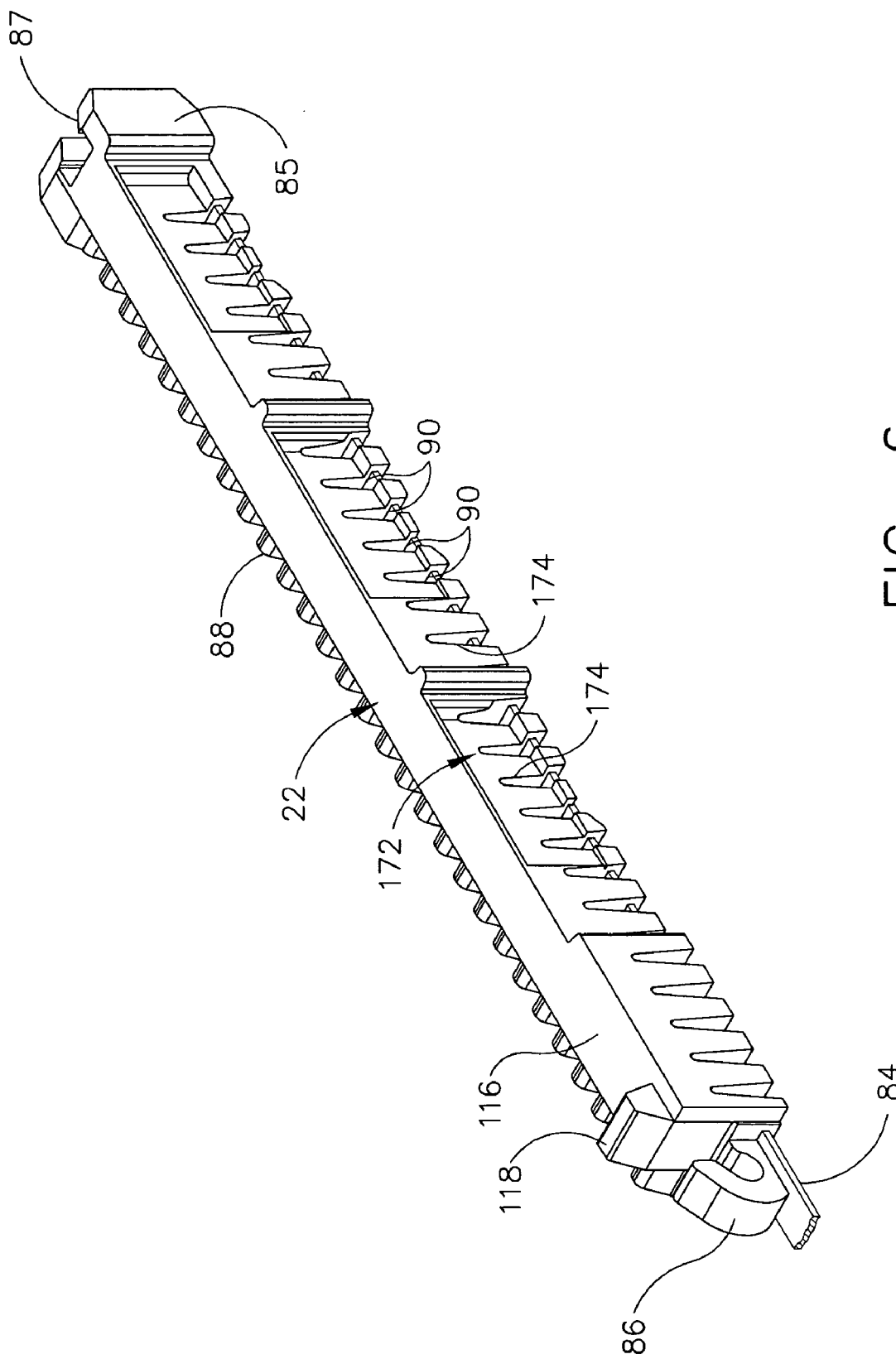
FIG. 6 is an aft right isometric view of the flexible firing rack of FIG. 2.
Figure 7:
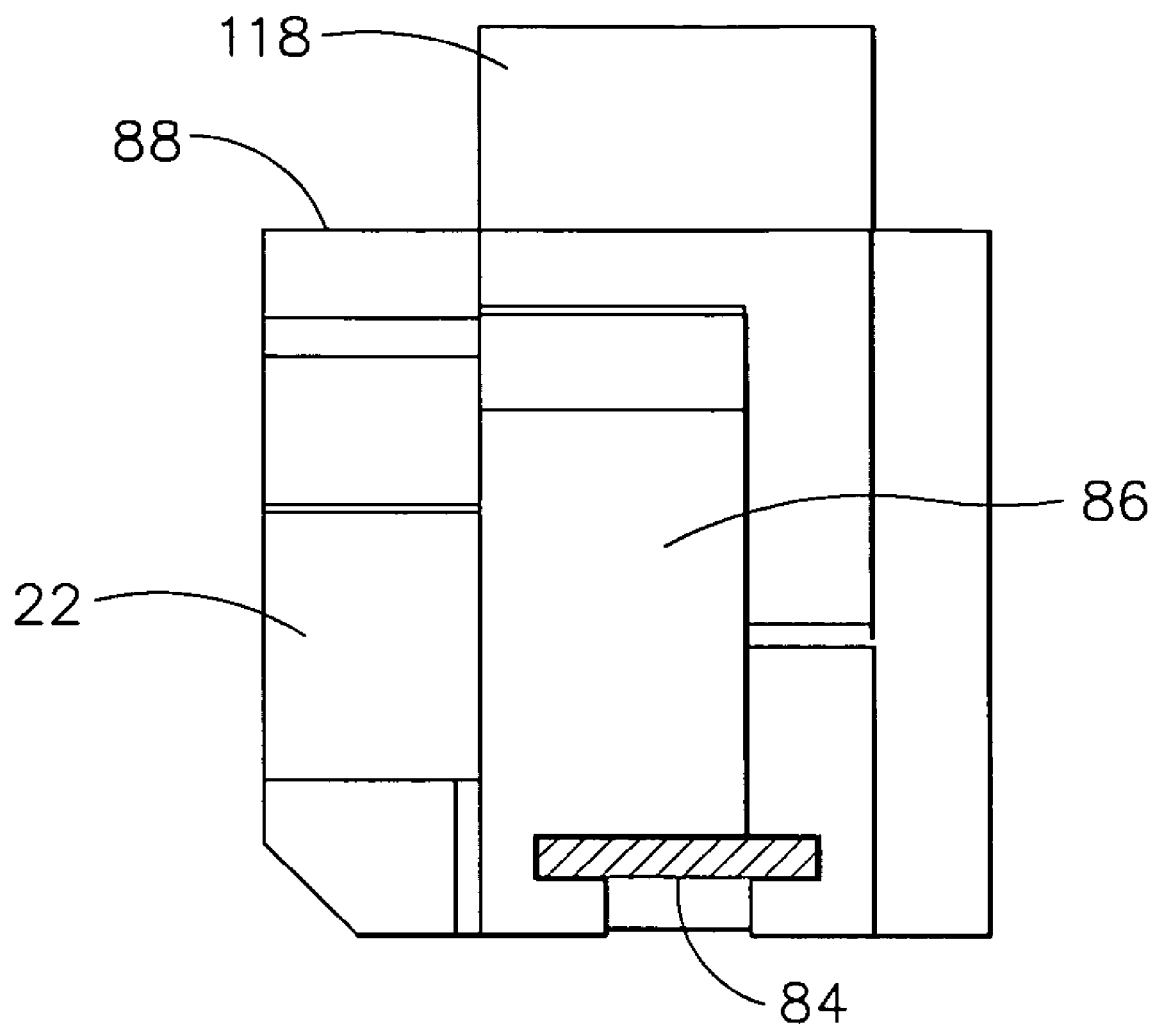
FIG. 7 is an aft view in elevation of the flexible firing rack of FIG. 2.

The flexible firing rack 22 is initially retracted, urged to remain in this position by a combination tension/compression spring 76 that is constrained within the pistol grip 27 of the handle 21, with its nonmoving end 78 connected to the housing 23 and a moving end 80 connected to a downwardly flexed and proximal, retracted end 82 of a steel band 84 that may be molded into the flexible firing rack 22 (FIGS. 6-7). Alternatively, the steel band 84 may underlie and attach to a front end 85 of the flexible firing rack 22 (FIG. 3). As a further alternative, a proximally presented hook 86 on the flexible firing rack 22 (FIGS. 4-5) may serve as an attachment for a retraction spring (not shown). In FIGS. 5-6, the front end 85 of the flexible firing rack 22 includes a female attachment receptacle 87 that engages a proximal end of the firing rod 72. A toothed rack segment 88 (FIGS. 2-5) is upwardly presented along a left edge of the flexible firing rack 22.

Figure 4:
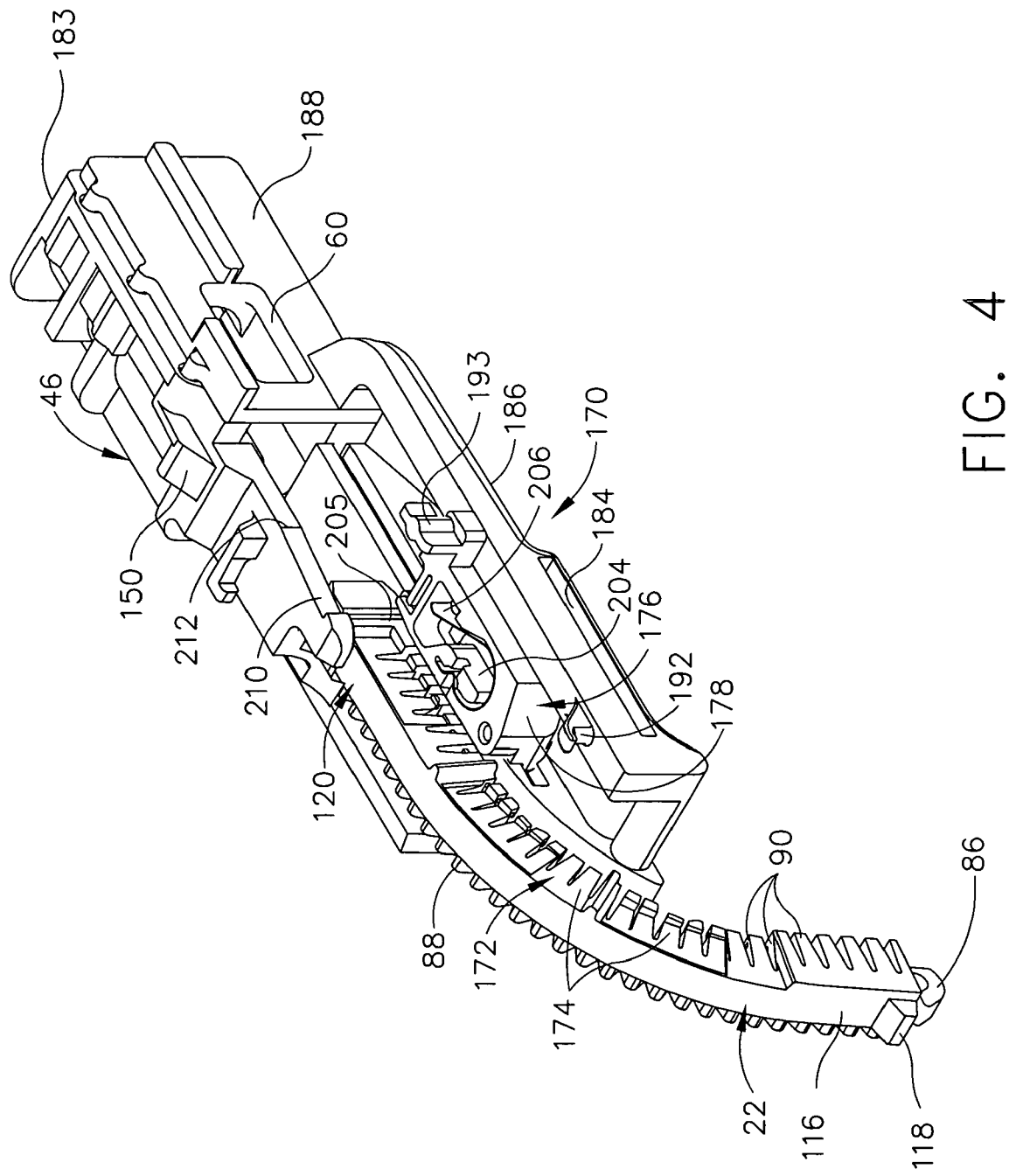
FIG. 4 is an aft right isometric view of the flexible firing rack and closure yoke of the surgical stapling and severing instrument of FIG. 2.

In FIGS. 4-6, in addition to incorporating a degree of downward flexibility into the flexible firing rack 22 by choice of material, a plurality of transverse slots 90 passing through a bottom portion accommodate the tighter radius of turn, enabling downward bending into the pistol grip 27, thereby minimizing the longitudinal length of the handle 21. Yet, the flexible firing rack 22 forms a sufficiently rigid rack structure in its upper portion when straightened by distal advancement into the closure yoke assembly 46 to transfer a significant firing force through the firing rod 72 in the implement portion 19, yet readily retracts into the pistol grip 27. It should be appreciated that the combination tension/compression spring 76 increases the amount of firing travel available while essentially reducing the minimum length by half over a single spring.

In FIG. 3, a distal pinion spur gear 91 engages the toothed rack segment 88, turned thereby during firing about a distal gear axle 92 whose lateral ends turn within receptacles in the handle half shells 56, 58. A proximal dual gear 93 has a left large spur gear 94 that is turned on axle 31 by the distal pinion spur gear 91. A coaxial right small ratchet gear 95 turns within a hub 96 that is attached to the manual firing release lever 34. A clip spring 97 urges a pawl 98 within the hub 96 into contact with the ratchet gear 95 so that actuation of the manual firing release lever 34 back drives the dual gear 93, the pinion spur gear 91, and the flexible firing rack 22 while an unlocking cam surface 99 unlocks an anti-backup mechanism 100.

With particular reference to FIGS. 2-3, the anti-backup mechanism 100 prevents the combination tension/compression spring 76 from retracting the flexible firing rack 22 between firing strokes. A coupling slide tube 101 has a proximally open cylindrical cavity 102 shaped to receive the front end 85 of the flexible firing rack 22 with a narrower distal opening 103 that allows passage of the firing rod 72 to communicate the firing motion. A pair of lateral recesses 104 proximally placed on the coupling slide tube 101 engage respectively the pair of closure yoke guide posts 59 that have passed into the closure yoke assembly 46 to ground the coupling slide tube 101. The firing rod 72 extends proximally out of a proximal end of the frame 40 and through a locking hole 105 of an anti-backup plate 106. The through hole 105 is sized to slidingly receive the firing rod 72 when perpendicularly aligned but to bind when tipped. A lower tab attachment 107 extends proximally from a lower lip of the proximal end of the frame 40, extending through an aperture 108 on a lower edge of an anti-backup plate 106. This lower tab attachment 107 draws the lower portion of the anti-backup plate 106 proximate to the frame 40 so that the anti-backup plate 106 is perpendicular when the firing rod 72 is distally advanced and allowed to tip top aft into a binding state when the firing rod 72 attempts to retract. An anti-backup compression spring 110 is distally constrained by the proximal end of the frame 40 and distally abuts a top portion of the anti-backup plate 106, biasing the anti-backup plate 106 to a locking state.

Opposing the aft bias from anti-backup compression spring 110, an anti-backup cam tube 112 slidingly encompasses the coupling slide tube 101 and abuts the anti-backup plate 106. A proximally projecting anti-backup yoke 114 attached to the anti-backup cam tube 112 extends overtop of the closure yoke assembly 46.

To cause knife retraction at the end of full firing travel, a proximal end 116 of the flexible firing rack 22 includes a tang 118 (FIGS. 4-5) that projects upwardly when the distal end 116 is advanced into a rack channel 120 formed in the closure yoke assembly 46. This tang 118 is aligned to activate a bottom proximal cam 122 on an anti-backup release lever 124. Alternatively or in addition, actuation of the manual release firing lever 34 distally moves the cam surface 99 on the hub 96 to distally move the bottom proximal cam 122 on the anti-backup release lever 124 to effect release. Structures formed in the right and left half shells 56, 58 constrain movement of the anti-backup release lever 124. A pin receptacle 126 and circular pin 128, formed respectively between right and left half shells 56, 58, is received through a longitudinally elongate aperture 130 formed in the anti-backup release lever 124 distal to the bottom proximal cam 122, thus allowing longitudinal translation as well as rotation about the circular pin 128. In the right half shell 56, a proximally open channel 132 includes a proximal horizontal portion that communicates with an upwardly and distally angled portion that receives a rightward aft pin 134 near the proximal end of the anti-backup release lever 124, thus imparting an upward rotation as the anti-backup release lever 124 reaches the distal most portion of its translation. A blocking structure 136, formed in the right half shell 56 proximal to the anti-backup release lever 124, prevents proximal movement thereof once assembled to maintain rightward aft pin 134 in the proximally open channel 132.

It should be appreciated that the rack channel 120 of the closure yoke assembly 46 serves as a longitudinally aligned firing member guide that stabilizes a distal portion of the flexible firing rack 22. In applications that do not include a distinct end effector closure mechanism, a longitudinally aligned firing member guide may be incorporated into the handle housing 23 as a stationary conduit.

A distal end 138 of the anti-backup release lever 124 thus is urged distally and downwardly, causing a rightward front pin 140 to drop into distally open step structure 142 formed in the right half shell 56, which is urged into this engagement by a compression spring 144 hooked to a leftward hook 146 on the anti-backup release lever 124 between the rightward front pin 140 and the longitudinally elongate aperture 130. The other end of the compression spring 144 is attached to a hook 148 formed in the left half shell 58 in a more proximal and lower position just above the closure yoke assembly 46. The compression spring 144 thus pulls the distal end 138 of the anti-backup release lever 124 down and aft, which results in the rightward front pin 140 locking into the distally open step structure 142 when distally advanced.

Once tripped, the anti-backup release lever 124 remains forward holding the anti-backup plate 106 perpendicularly, thus allowing the flexible firing rack 22 to be retracted. When the closure yoke assembly 46 is subsequently retracted when unclamping the end effector 12, an upwardly projecting reset tang 150 on the closure yoke assembly 46 contacts a bottom distal cam 152 of the anti-backup release lever 124, lifting the rightward front pin 140 out of the distally open step structure 142 so that the anti-backup compression spring 110 can proximally push the anti-backup cam tube 112 and the anti-backup release lever 124 to their retracted positions. To effect the distal movement of the flexible firing rack 22, the firing trigger 30 pivots about the firing trigger pin 74 that is connected to the housing 23. An upper portion 160 of the firing trigger 30 moves distally about the firing trigger pin 74 as the firing trigger 30 is depressed towards pistol grip 27, stretching a proximally placed firing trigger tension spring 162 proximally connected between a spring pin 163 attached to the upper portion 160 of the firing trigger 30 and the housing 23.

In FIGS. 2-4, the upper portion 160 (FIGS. 2-3) of the firing trigger 30 engages the flexible firing rack 22 during each firing trigger depression by a side pawl mechanism 170 that also disengages when the firing trigger 30 is released. In particular, a ramped right-side track 172 formed by a plurality of proximally and rightwardly facing beveled surfaces 174 spaced along the flexible firing rack 22 are sequentially engaged by a side pawl slide assembly 176. In particular, a pawl slide block 178 has right and left lower guides 180 that slide respectively in a left track 182 formed in a main body 183 of the closure yoke assembly 46 below the rack channel 120 and a right track 184 in a closure yoke rail 186 that parallels rack channel 120 and is attached to a rack channel cover 188 that closes a rightwardly open portion of the rack channel 120 in the main body 183 of the closure yoke assembly 46 that is distal to the travel of the pawl slide assembly 176. A compression spring 190 is attached between a hook 192 on a top proximal position on the closure yoke rail 186 and a hook 193 on a distal right side of the pawl slide block 178, which keeps the pawl slide block 178 drawn proximally into contact with the upper portion 160 of the firing trigger 30.

A pawl block 194 sits on the pawl slide 178 pivoting about a vertical aft pin 196 that passes through a left proximal corner of pawl block 194 and pawl slide 178. A kick-out block recess 198 is formed on a distal portion of a top surface of the block 194 to receive a kick-out block 200 pivotally pinned therein by a vertical pin 202 whose bottom tip extends into a pawl spring recess 204 on a top surface of the pawl slide 178. A pawl spring 206 in the pawl spring recess 204 extends to the right of the vertical front pin 202 urging the pawl block 194 to rotate counterclockwise when viewed from above into engagement with the ramped right-side track 172. A small coil spring 208 in the kick-out block recess 198 urges the kick-out block 200 to rotate clockwise when viewed from above, its proximal end urged into contact with a contoured lip 210 formed in the closure yoke assembly 46 above the rack channel 120.

It should be appreciated that the stronger mechanical advantage of the pawl spring 206 over the small coil spring 208 means that the pawl block 194 tends toward engagement with the kick-out block 200 rotated clockwise. As the firing trigger 30 is fully depressed and begins to be released, the kick-out block 200 encounters a ridge 212 (FIG. 4) in the contoured lip 210 as the pawl slide 178 retracts, forcing the kick-out block 200 to rotate clockwise when viewed from above and thereby kicking out the pawl block 194 from engagement with the flexible firing rack 22. The shape of the kick-out block recess 198 stops the clockwise rotation of the kick-out block 200 to a perpendicular orientation to the contoured lip 210 maintaining this disengagement during the full retraction and thereby eliminating a ratcheting noise. The selection of the material of the flexible firing rack 22 may further dampen ratcheting noise.

Figure 8:
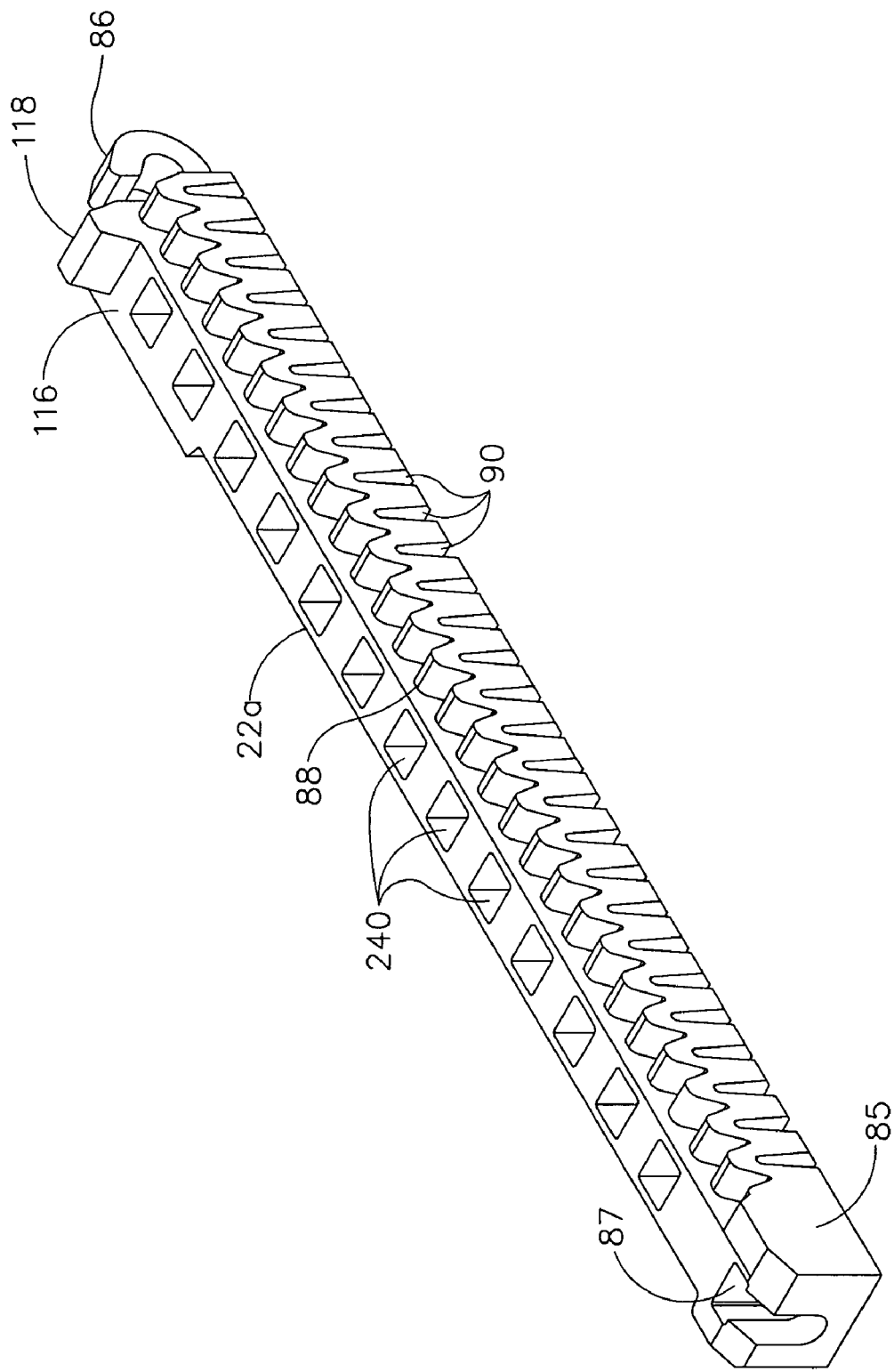
FIG. 8 is a front left isometric view of an alternative flexible firing rack with top apertures for the surgical stapling and severing instrument of FIG. 1.

In FIG. 8, an alternative flexible firing rack 22a with longitudinally aligned rectangular top apertures 240 along a right portion of a top surface reduces rigidity enhancing downward flexing for stowing in the pistol grip 27 of the surgical stapling and severing instrument 10 (FIG. 1).

Figure 9:
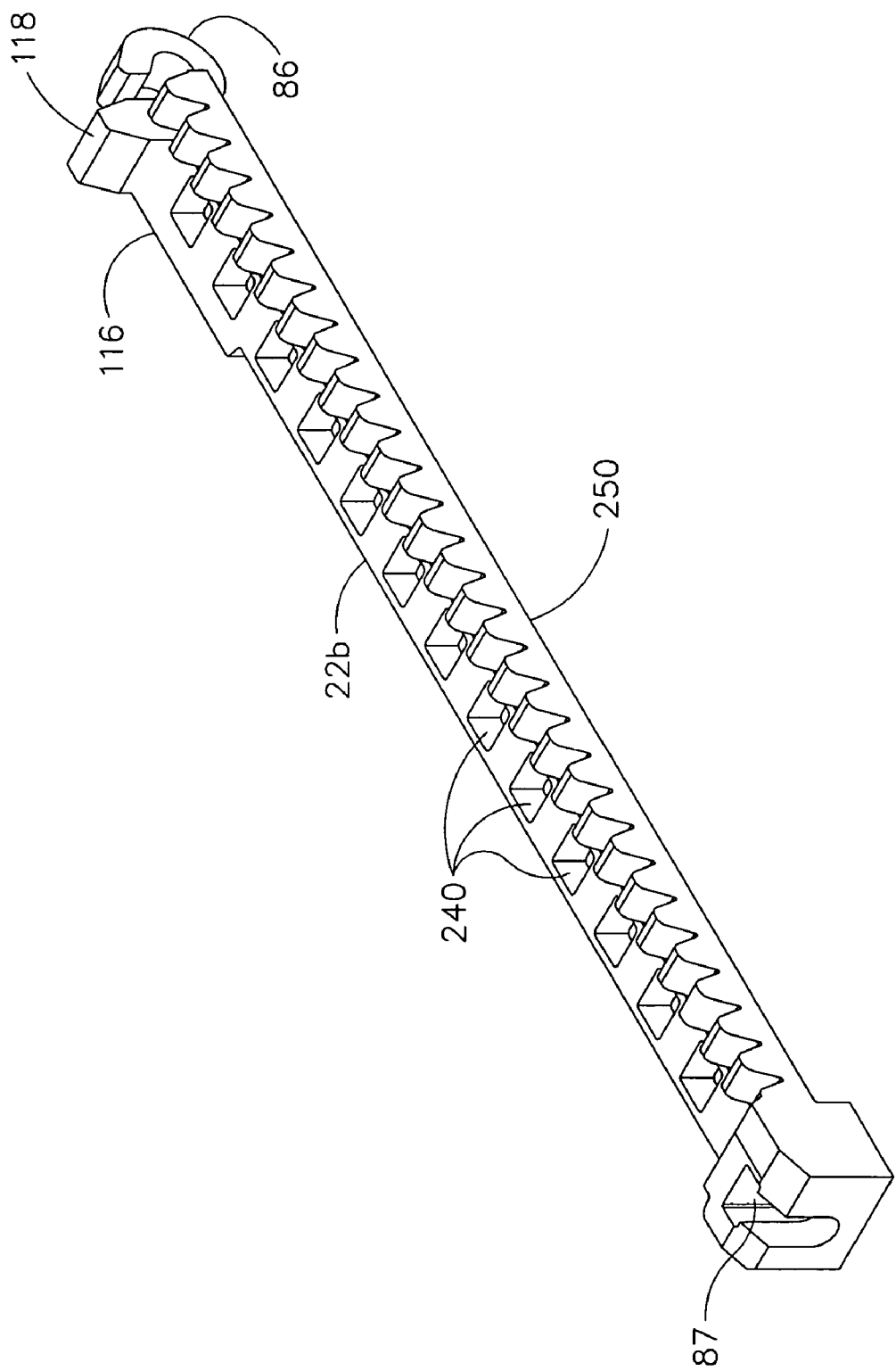
FIG. 9 is a front left isometric view of another alternative flexible firing rack with sprocket holes for manual retraction for the surgical stapling and severing instrument of FIG. 1.

In FIG. 9, another alternative flexible firing rack 22b includes the top apertures 240 and in addition includes a bottom relieved portion 250 rather than traverse slots 90 to enhance downward flexibility.

In FIGS. 10-17, an alternative surgical stapling and severing instrument 10' is as described above for FIGS. 1-4 with the exception of substitution of a linked rack 22c, similar to that described in the afore-referenced U.S. Pat. No. 6,905,057 instead of the flexible firing rack 22, 22a-22b. In addition, rather than the afore-described side pawl mechanism 170, a chain drive 170a fires the linked rack 22c.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Figure 12:
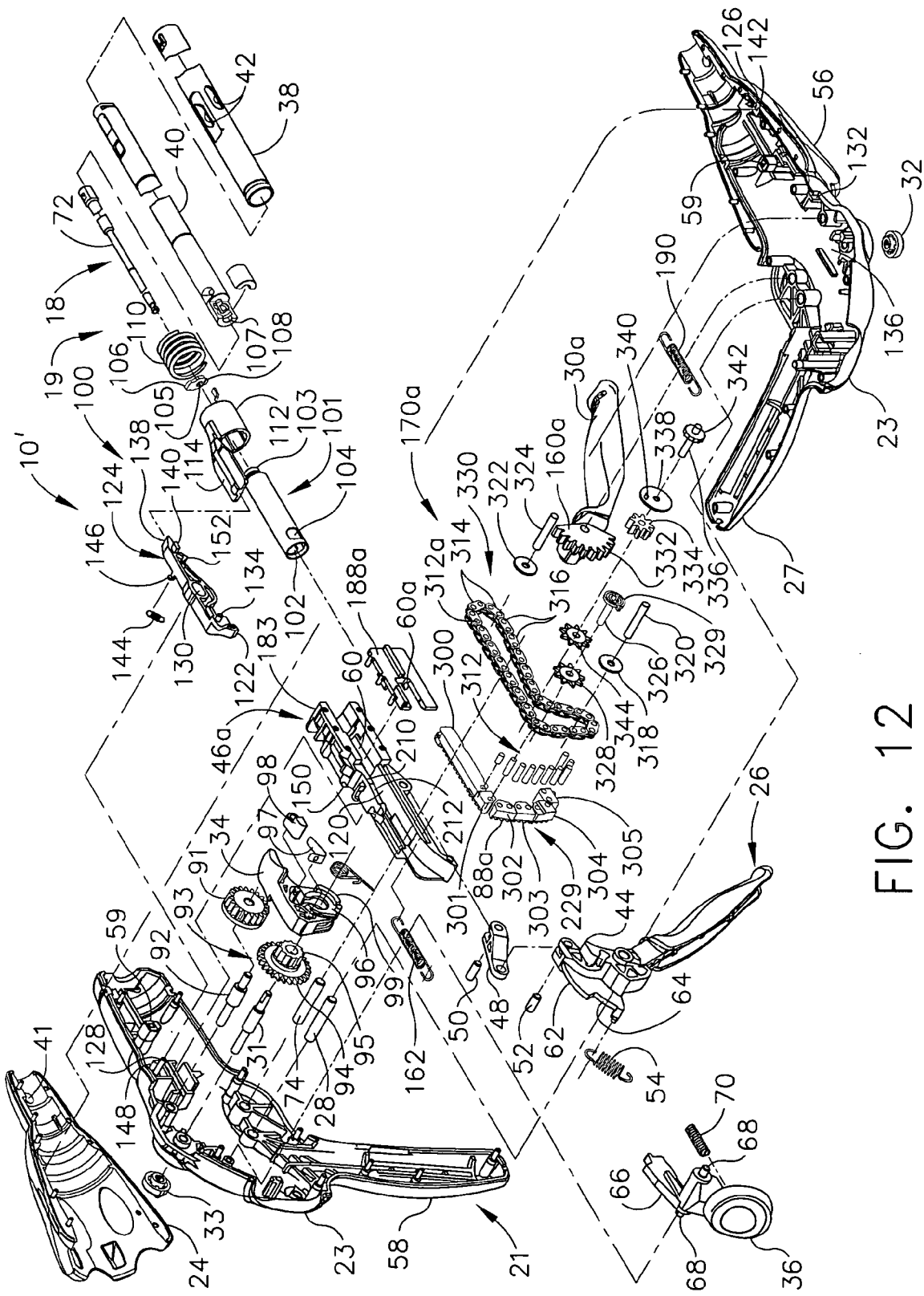
FIG. 12 is an aft right isometric exploded view of the alternative surgical stapling and severing instrument of FIG. 10 with the staple applying assembly omitted.
Figure 13:
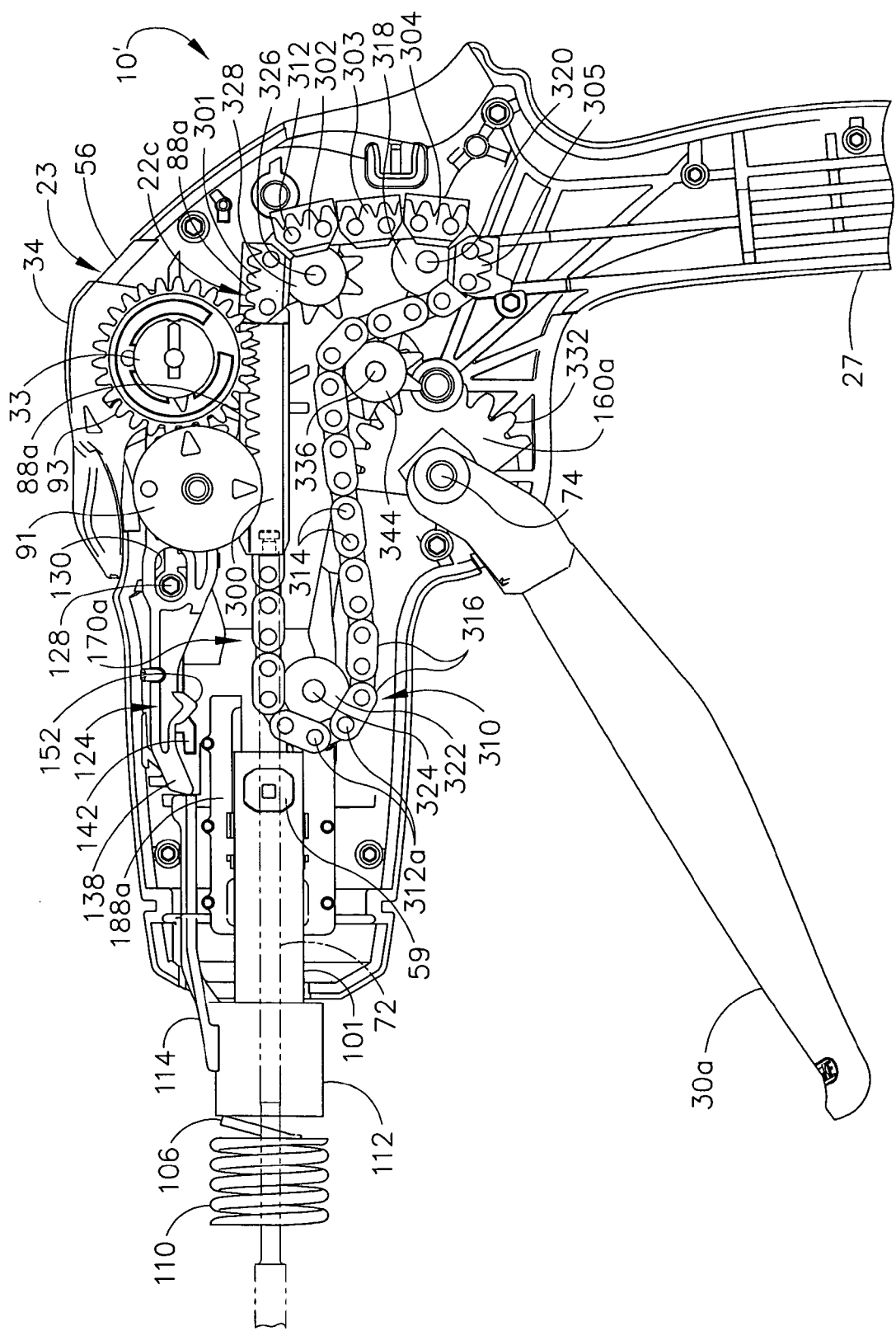
FIG. 13 is a left side view in elevation of a handle of the alternative surgical stapling and severing instrument of FIG. 10 with the right handle shell, main body of the closure yoke assembly, rotation knob, closure tube and closure trigger omitted to expose a closure yoke distally advanced (i.e., closed end effector) and the loop chain drive and linked rack in an initial, unfired state.
Figure 14:
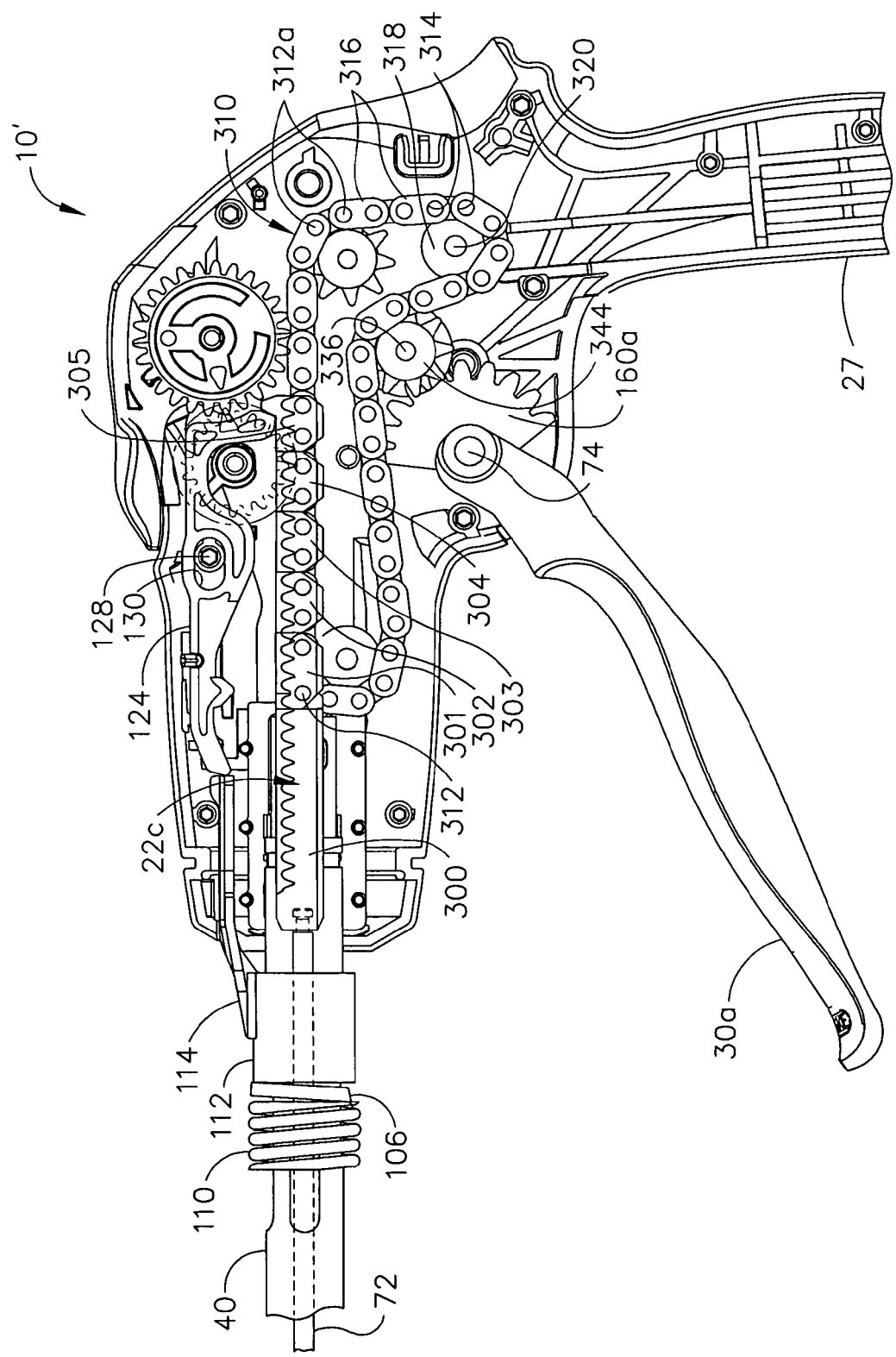
FIG. 14 is a left side view in elevation of the portion of the handle of the alternative surgical stapling and severing instrument of FIG. 13 after the loop chain drive has moved the linked rack to a fired state.
Figure 15:
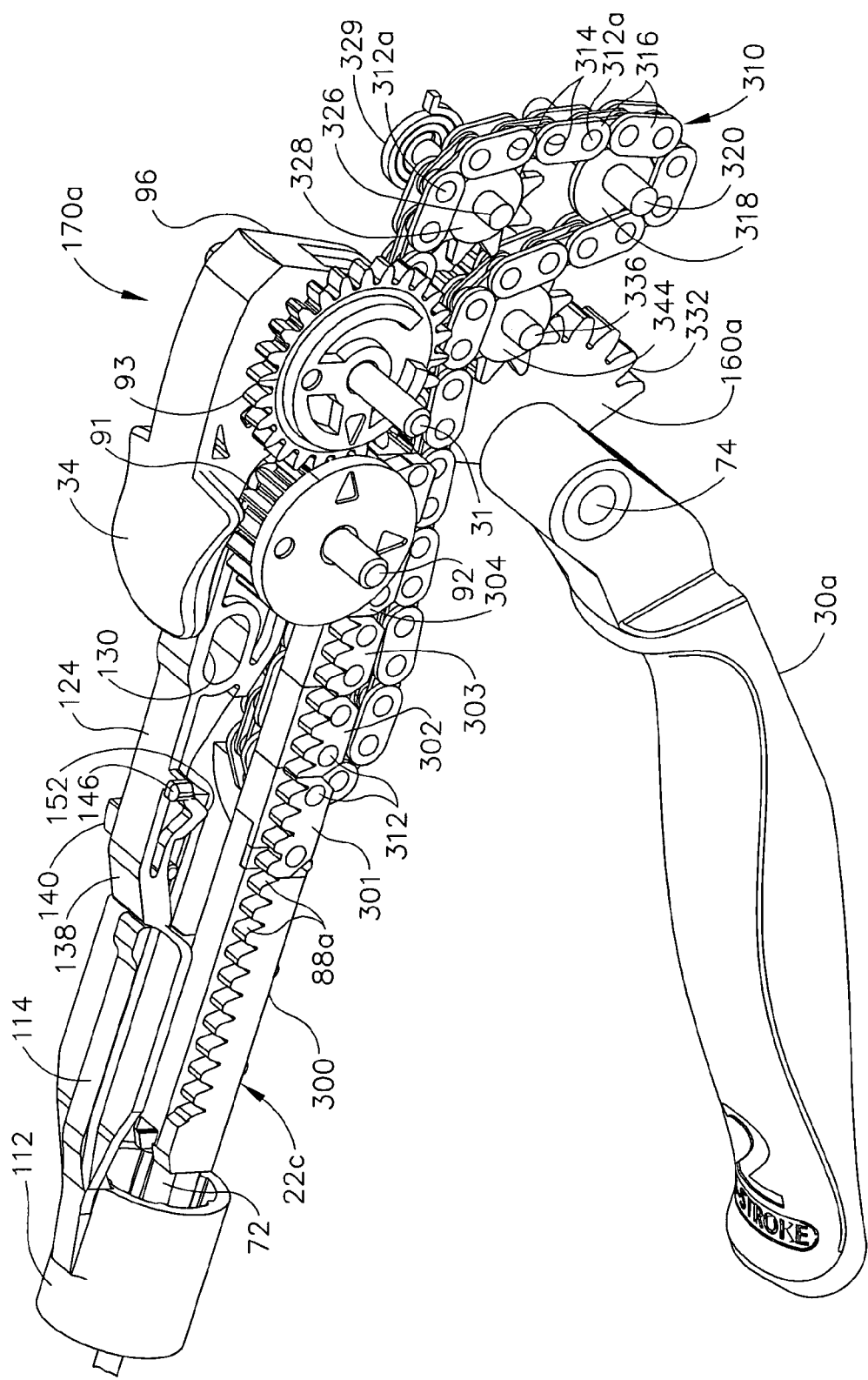
FIG. 15 is an aft left isometric view of the firing trigger, loop chain drive, linked rack and manual retraction mechanism of the portion of the handle of FIG. 14.
Figure 16:
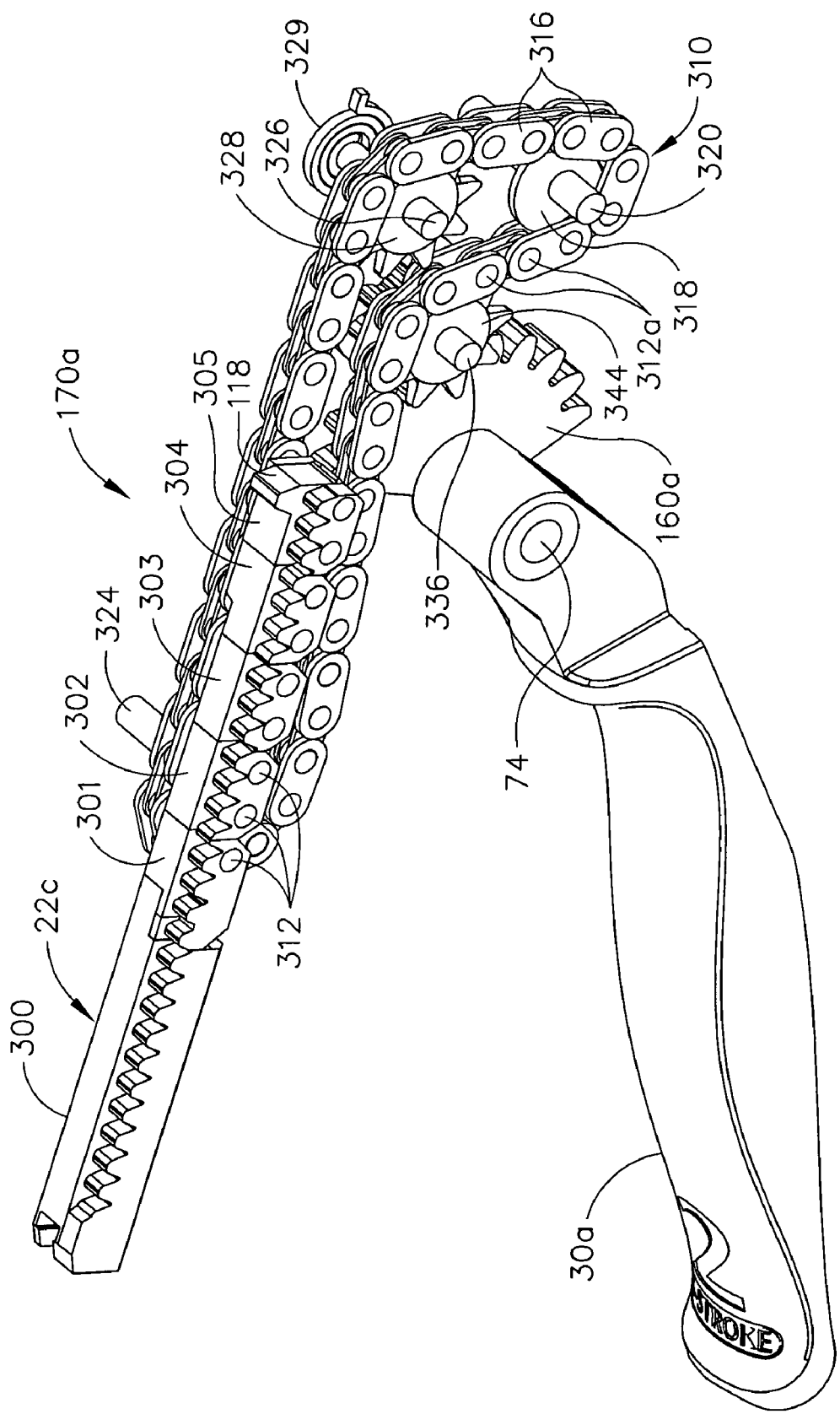
FIG. 16 is an aft left isometric view of the firing trigger, loop chain drive, and linked rack of FIG. 15.
Figure 17:
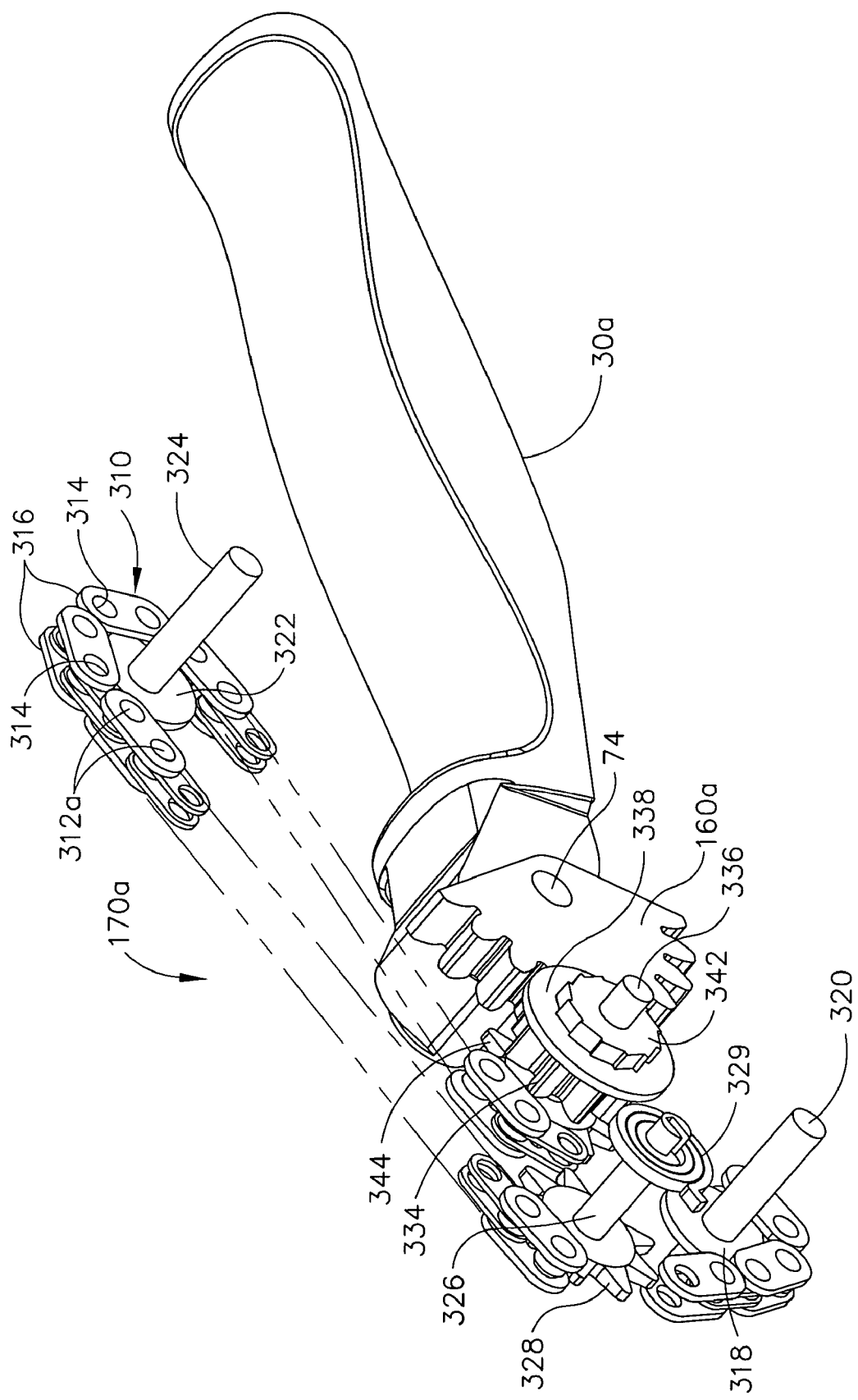
FIG. 17 is an aft right isometric exploded isometric view of the loop chain drive of FIG. 16 including a ratchet gear coupling to the firing trigger.

With particular reference to FIG. 12, the linked rack 22c includes a distal long link 300 that reciprocates within the rack channel 120 of a closure yoke assembly 46a, the latter differing in that the main body 183 is attached to a right-side rack channel cover 188a that includes a recess 60a that engages the right side closure yoke guide post 59 of the right half shell 56. A plurality of smaller rack links 301-305 proximal to the distal long link 300 have rounded adjacent ends that allow for the links 301-305 to rotate downwardly yet present a respective portion of a toothed rack segment 88a when in the rack channel 120. Each link 300-305 is engaged to a looped bicycle-style drive chain 310 by a respective pair of long pins 312 that pass through chain link pivot holes 314 through a respective chain link 316 of the drive chain 310. Other chain links 316 are pinned together by short link pins 312a.

A lower proximal idler wheel 318 rotates upon an axle 320 in an aft portion of the handle housing 23 adjacent to the closure release button 36 and to the right half shell 56. A distal idler wheel 322 rotates upon an axle 324 proximal to a retracted position of the rack channel cover 188a. The drive chain 310 rotates at each looped end about these idler wheels 318, 322. Above the lower proximal idler wheel 318, an axle 326 passes within the drive chain 310 so that a retraction bias spur gear 328, rotating about the axle 326, engages and forms an approximately 90 degree corner in the drive chain 310. A coil spring 329 has an inner end attached to the retraction bias spur gear 328 and an outer end attached to the right half shell 56 and is wound such that clockwise (when viewed from the right) firing of the drive chain 310 tightens the coil spring 329, providing a retraction bias to the chain drive 170a.

A firing trigger 30a has an upper portion 160a that is coupled during each firing depression by a firing trigger ratchet assembly 330. In particular, arcing gear teeth 332, which are radially equidistant from the firing trigger axle 74, engage a trigger spur gear 334 that free wheels on a ratchet axle 336. A disk 338 that is attached to a right side of the trigger spur gear 334 also freely rotates on the ratchet axle 336 and presents a ratchet pawl 340 to a ratchet gear 342 that is attached to rotate with the ratchet axle 336. A spur gear 344 is also attached to rotate with the ratchet axle 336 and is positioned under the chain drive 310 to engage the chain drive 310 and constrain its movement into a dogleg shape. The ratchet gear 342 (FIG. 11) is shaped such that the firing trigger ratchet assembly 330 converts the clockwise rotation (CW) (when viewed from the right) of the arcing gear teeth 332 and thus counter clockwise rotation (CCW) of the trigger spur gear 334 into a CCW rotation of the ratchet axle 336 and spur gear 344 and thus the drive chain 310. Forming the disk 338 and ratchet pawl 340 from a molded polymer may advantageously provide economy for a surgical stapling and severing instrument of limited operational life as well as reducing ratchet noise.

Figure 10:
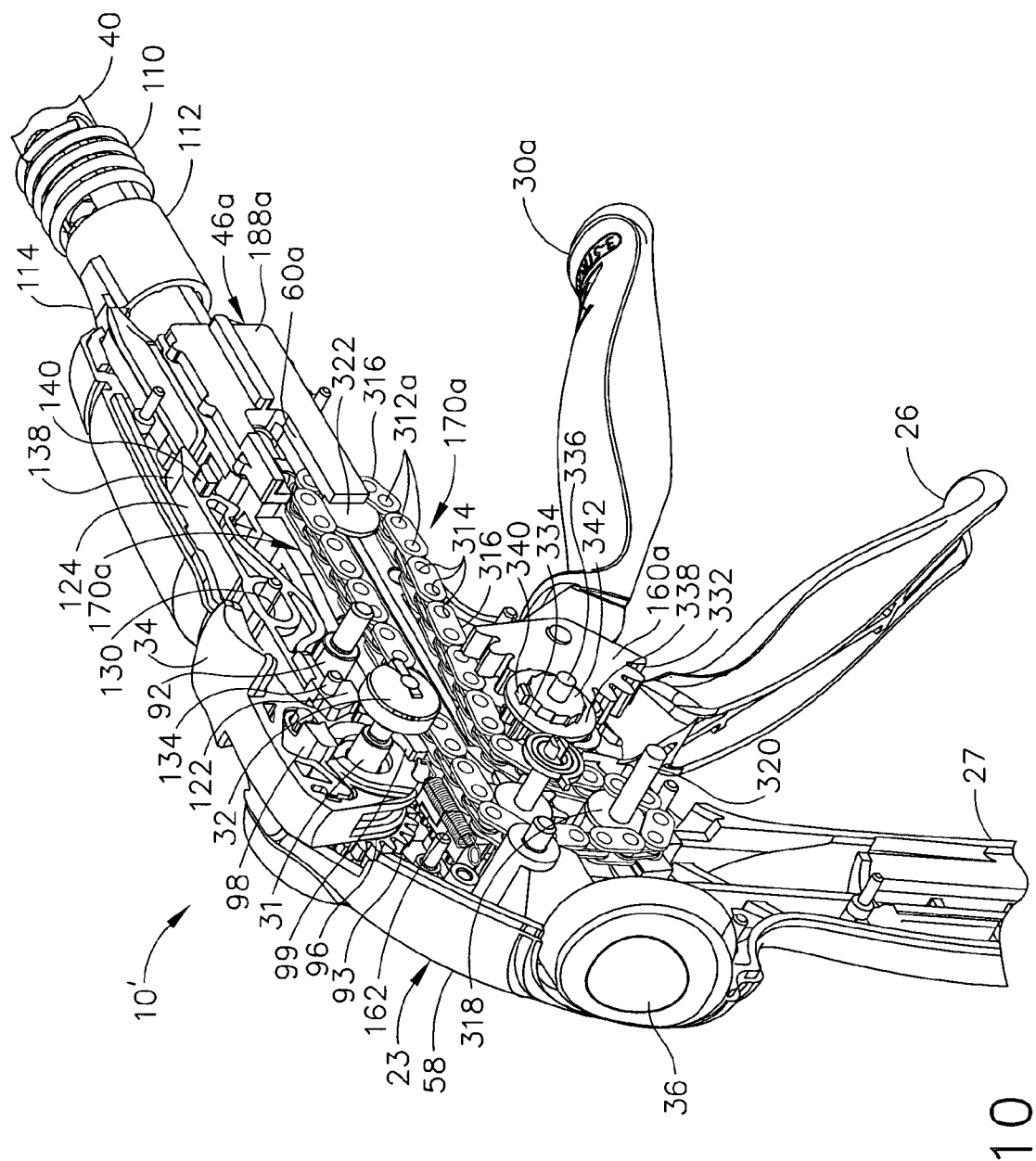
FIG. 10 is an aft right isometric view of an alternative surgical stapling and severing instrument with a right handle shell and rotation knob omitted to expose a loop chain drive and a linked rack in an initial state.
Figure 11:
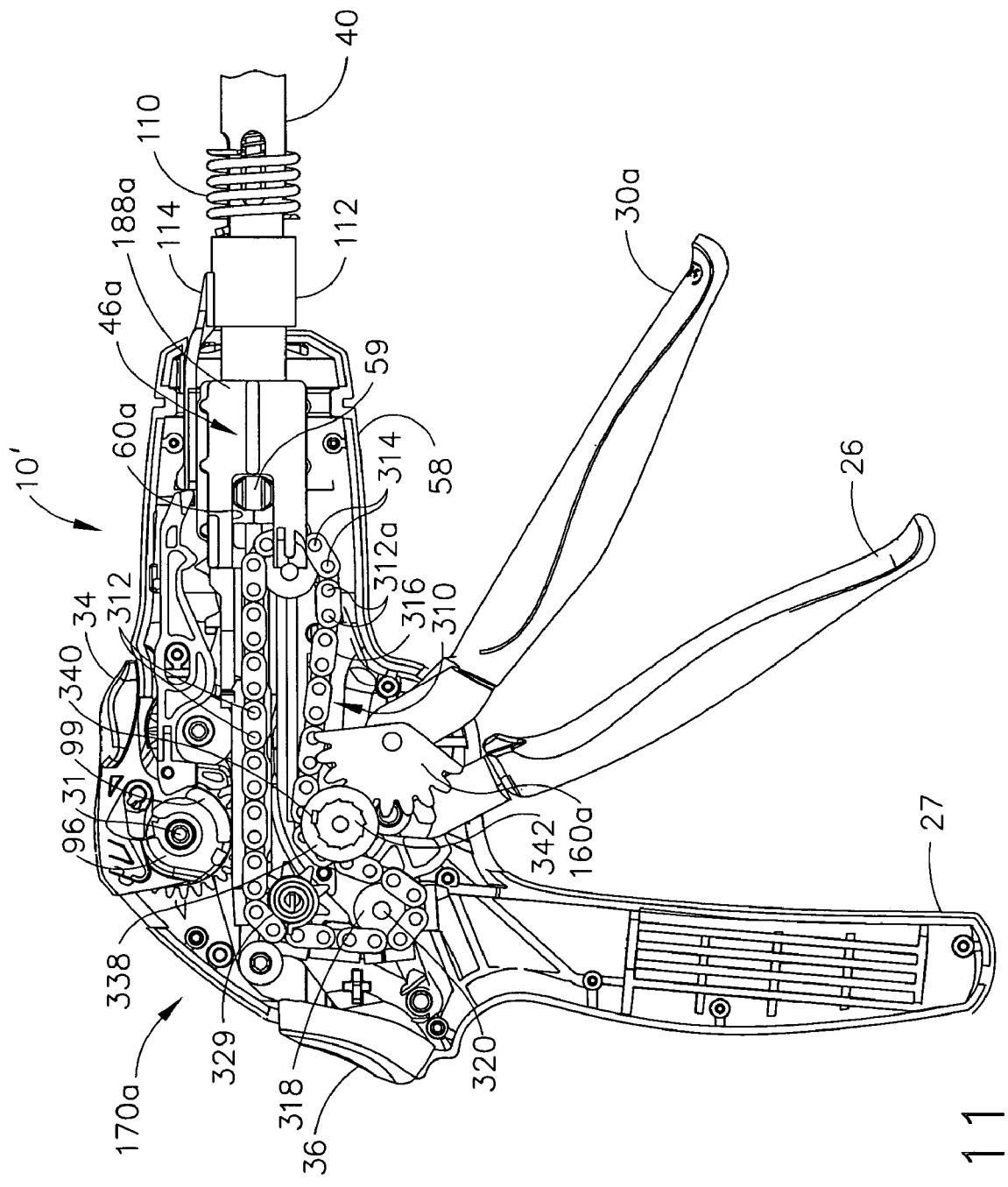
FIG. 11 is a right side view in elevation of the alternative surgical stapling and severing instrument of FIG. 10 with the right handle shell and rotation knob omitted.

In use, the surgical stapling and severing instrument 10' is initially unclamped and unfired in FIGS. 10-11. Once clamped, the firing trigger 30a is depressed a plurality of times, moving the linked rack 22c from a retracted position (FIG. 13) to a distally fired position (FIGS. 14-15) by the chain drive 170a. In particular, the firing trigger ratchet assembly 330 allows the firing trigger 30a to distally advance the top portion of a drive chain 310, which winds the retraction coil spring 329. The anti-backup mechanism 100 is tripped after full firing travel by the tang 118 on the most proximal link 305 contacting the anti-backup release lever 124. The firing trigger ratchet assembly 330 allows the drive chain 310 to be rotated in a retraction direction without coupling to the firing trigger 30a. Alternatively, the manual retraction release lever 34 may be actuated, moving the anti-backup release lever 124 to a released position and backdriving gears 93, 91 that retract the linked rack 22c by engaging the tooth rack segment 88a.

In FIGS. 18A-18D, a flexible threaded cable firing mechanism 400 for an additional alternative surgical stapling and severing instrument 10" advantageously enables a length of firing travel that would not necessarily require a longer handle. In FIG. 18A, distal and proximal handle grounding structures 402, 404 encompass a cylindrical firing sleeve 406 that has a central bore 408 including an inner diameter (ID) threaded portion 410 along a distal end 412 that includes an increased diameter distal head 414 that initially abuts the distal handle grounding structure 402. A central portion 416 of the cylindrical firing sleeve 406 has a constant radius for reciprocally sliding a small amount through the distal and proximal handle ground structures 402, 404. A proximal hub end 418 of the cylindrical firing sleeve 406 has a slightly increased radius that is initially spaced proximally from the proximal handle grounding structure 404 and may be moved into abutment with the same. A compression spring 420 encompasses the central portion 416 of the cylindrical firing sleeve 406, contacting a proximal surface of the distal handle grounding structure 402 and a distal surface of an aft directed bevel gear 422 encompassing and attached to the central portion 416 of the cylindrical firing sleeve 406, providing a proximal bias to the cylindrical firing sleeve 406.

A flexible rod 424 passes through the central bore 408 and includes outer diameter (OD) threads 426 that engage the ID threaded portion 410 of the cylindrical firing sleeve 406. A cable coupling 428 is attached at its proximal end to the flexible rod 424 and at its distal end to the firing rod 72. An anti-rotation pin 430 extends laterally from the cable coupling 428 to longitudinally slide along a pin guide 432 grounded to the handle (not shown) while preventing rotation of the flexible rod 424. A cable sheath 433 for reduced friction may cover a portion of the flexible rod 424 proximal to a portion that is capable of reaching the ID threaded portion 410.

A left bevel gear 434 is coupled by a one-way clutch (e.g., ratchet) to a firing trigger (not shown) to turn the aft directed transverse bevel gear 422 and thus the cylindrical firing sleeve 406 in a first direction. Given the corresponding direction of turns of the threads 410, 426, the flexible rod 424 distally translates from the cylindrical firing sleeve 406, distally moving the cable coupling 428 and the firing rod 72.

The rotation in the first direction of the cylindrical firing sleeve 406 winds a retraction coil spring 436 that encompasses and has an inner end attached to a distal portion of the proximal hub end 418 and has an outer end 437 (FIG. 18D) grounded to the handle housing (not shown). Between firing strokes when the firing trigger is uncoupled from the left bevel gear 434, the retraction coil spring 436 is prevented from turning the cylindrical firing sleeve 406 in the opposite second direction by a ratchet mechanism 438. In particular, a ratchet gear 440 encompassing a central portion of the proximal hub end 418 is form proximally adjacent to the retraction coil spring 436. A most proximal lateral surface 442 has a reduced radius. A pawl 444 is grounded to the handle (not shown). With the cylindrical firing sleeve 406 retracted as in FIG. 18A, the pawl 444 engages the ratchet gear 440 preventing rotation in the second direction.

In FIG. 18B, as the flexible rod 424 approaches full distal travel, a cable stop 446 attached to the flexible rod 424 distally advances sufficiently to contact the proximal surface of the cylindrical firing sleeve 406, translating the cylindrical firing sleeve 406 distally and compressing the compression spring 420. The increased diameter distal head 414 contacts a distally ramped proximal edge 448 of a rocker latch 450 that pivots about pivotal connection 452 grounded to the housing (not shown). It should be appreciated that the rocker latch 450 is biased inwardly and thus the ramped proximal catch 448 rotates to longitudinally capture a proximal edge of the increased diameter distal head 414 of the cylindrical firing sleeve 406. Distal translation of the cylindrical firing sleeve 406 moves the ratchet gear 440 out from under the ratchet pawl 444 allowing the retraction coil spring 436 to rotate the cylindrical firing sleeve 406 in the second direction, which in turn retracts the flexible rod 424. In FIG. 18C, the cable coupling 428 has retracted sufficiently to contact a proximally ramped release arm 454 of the rocker latch 450, rotating the ramped proximal catch 448 out of engagement with the increased diameter distal 414 of the cylindrical firing sleeve 406 and allowing the compression spring 420 to urge the cylindrical firing sleeve 406 proximally, resetting the mechanism 400 to the state of FIG. 18A.

A right bevel gear 456 may be included that is part of a manual firing release mechanism 458 that releases the ratchet mechanism 438 (e.g., distally shifts cylinder firing sleeve 406, displaces ratchet pawl 444) and rotates the cylinder firing sleeve to retract the flexible rod 424. The right bevel gear 456 may include a pivot bias (not shown) that normally maintains the right bevel gear 456 out of contact with the aft directed transverse bevel gear 422, whether retracted as in FIG. 18A or extended as in FIG. 18B, but which distally translates the right bevel gear 456 sufficiently for engagement when a manual firing retraction lever (not shown in FIGS. 18A-D) is actuated.

While the present invention has been illustrated by description of several embodiments and while the illustrative embodiments have been described in considerable detail, it is not the intention of the applicant to restrict or in any way limit the scope of the appended claims to such detail. Additional advantages and modifications may readily appear to those skilled in the art.

For example, while the additional firing travel typical of multiple firing strokes illustrates particular advantages of a flexible firing member contained in the handle, it should be appreciated that aspects of the present invention may be applied to single firing stroke instruments.

For another example, while a transverse cavity afforded by a pistol grip illustrates one location to retract a flexible firing member, applications consistent with the present invention may not include a pistol grip. For instance, the flexible firing member may be routed around a 180 degree bend with a retracted end closely parallel to a distal end.

For yet another example, while a manually actuated firing trigger is illustrated for clarity, remotely actuated handles may benefit from a flexible firing member incorporated into a proximal portion equivalent to a handle that is positioned and/or held by a fixture or robotic manipulator.

What is claimed is:

1. A surgical instrument, comprising:
    an end effector responsive to a longitudinal firing motion to perform a surgical operation;
    a shaft distally connected to the end effector;
    a shaft firing member slidingly received by the shaft to transfer the firing motion to the end effector; and
    a handle proximally connected to the shaft and firing member, comprising:
        a flexible firing member having a distal end coupled to a proximal end of the shaft firing member, wherein the flexible firing member comprises an articulated plurality of links,
        a firing actuator reciprocally positioned by an operator to distally translate a distal portion of the flexible firing member, and
        a handle housing comprising a barrel portion positioned to guide the distal portion of the flexible firing member and comprising a stowage area communicating with the barrel portion and positioned to guide a deflected proximal portion of the flexible firing member during retraction.

2. The surgical instrument of claim 1, wherein the flexible firing member comprises an elastomeric material.

3. The surgical instrument of claim 2, wherein the flexible firing member further comprises a recess portion aligned for downward deflection.

4. The surgical instrument of claim 2, wherein the flexible firing member further comprises a plurality of longitudinally aligned recesses along a top portion for downward deflection.

5. The surgical instrument of claim 1, further comprising a drive chain mechanism operatively configured to couple the firing actuator to the flexible firing member.

6. The surgical instrument of claim 1, further comprising a manual firing release mechanism operatively configured to retract the flexible firing member.

7. The surgical instrument of claim 1, wherein the stowage area comprises a pistol grip.

8. The surgical instrument of claim 1, wherein the handle further comprises a longitudinally aligned firing member guide aligned with a proximal portion of the shaft firing member, the firing actuator reciprocally positioned by an operator to distally translate a distal portion of the flexible firing member into the longitudinally aligned firing member guide.

9. The surgical instrument of claim 1, further comprising:
    an implement portion responsive to longitudinal firing motion and diametrically dimensioned for endo-surgical use, the implement portion comprising:
        the shaft;
        the shaft firing member slidingly received by the shaft to transfer the firing motion;
        an elongate channel coupled to the shaft; and
        the end effector responsive to the longitudinal firing motion to perform the surgical operation, comprising an anvil pivotally coupled to the elongate channel, responsive to the closing motion from the shaft, and including an anvil channel, a firing bar attached to the firing member and including a distally presented cutting edge longitudinally received between the elongate channel and the anvil, and a staple device received in the elongate channel and responsively coupled to the firing bar to form staples against the anvil.

10. The surgical instrument of claim 9, wherein the shaft further comprises a closure sleeve attached to pivot the anvil, the handle further comprises a closure trigger, and the longitudinally aligned firing member guide comprises a closure yoke distally positioned by the closure trigger to translate the closure sleeve.

11. A surgical instrument, comprising:
an end effector responsive to a longitudinal firing motion to perform a surgical operation;
a shaft distally connected to the end effector;
a shaft firing member slidingly received by the shaft to transfer the firing motion to the end effector; and
a handle proximally connected to the shaft and firing member, comprising:
a flexible firing member having a distal end coupled to a proximal end of the shaft firing member,
a firing actuator reciprocally positioned by an operator to distally translate a distal portion of the flexible firing member, and
a handle housing comprising a barrel portion positioned to guide the distal portion of the flexible firing member and comprising a stowage area communicating with the barrel portion and positioned to guide a deflected proximal portion of the flexible firing member during retraction,
wherein the flexible firing member comprises an elastomeric material, a recess portion aligned for downward deflection, and wherein the recess portion in turn comprises a plurality of transverse slots passing perpendicularly to a longitudinal axis of and passing through a lower portion of the flexible firing member.

12. A surgical instrument, comprising:
an end effector responsive to a longitudinal firing motion to perform a surgical operation;
a shaft distally connected to the end effector;
a shaft firing member slidingly received by the shaft to transfer the firing motion to the end effector; and
a handle proximally connected to the shaft and firing member, comprising:
a flexible firing member having a distal end coupled to a proximal end of the shaft firing member, wherein the flexible firing member further comprises a toothed gear rack segment,
a firing actuator reciprocally positioned by an operator to distally translate a distal portion of the flexible firing member, and
a handle housing comprising a barrel portion positioned to guide the distal portion of the flexible firing member and comprising a stowage area communicating with the barrel portion and positioned to guide a deflected proximal portion of the flexible firing member during retraction.

13. A surgical instrument, comprising:
an end effector responsive to a longitudinal firing motion to perform a surgical operation;
a shaft distally connected to the end effector;
a shaft firing member slidingly received by the shaft to transfer the firing motion to the end effector; and
a handle proximally connected to the shaft and firing member, comprising:
a flexible firing member having a distal end coupled to a proximal end of the shaft firing member
a firing actuator reciprocally positioned by an operator to distally translate a distal portion of the flexible firing member, and
a handle housing comprising a barrel portion positioned to guide the distal portion of the flexible firing member and comprising a stowage area communicating with the barrel portion and positioned to guide a deflected proximal portion of the flexible firing member during retraction;
wherein the flexible firing member further comprises a longitudinally aligned plurality of ramped recesses, the handle further comprising a pawl mechanism positioned by the firing actuator to engage a selected one of the plurality of ramped recesses and thereby distally transfer the flexible firing member.

14. A surgical instrument, comprising:
an end effector responsive to a longitudinal firing motion to perform a surgical operations
a shaft distally connected to the end effector;
a shaft firing member slidingly received by the shaft to transfer the firing motion to the end effector; and
a handle proximally connected to the shaft and firing member, comprising:
a flexible firing member having a distal end coupled to a proximal end of the shaft firing member,
a firing actuator reciprocally positioned by an operator to distally translate a distal portion of the flexible firing member, and
a handle housing comprising a barrel portion positioned to guide the distal portion of the flexible firing member and comprising a stowage area communicating with the barrel portion and positioned to guide a deflected proximal portion of the flexible firing member during retraction;
wherein the flexible firing member further comprises a spring attachment, the handle further comprising a retraction spring attached to the handle housing in the stowage area and attached to the spring attachment on the firing member to bias the flexible firing member into the stowage area.

15. A surgical instrument, comprising:
an end effector responsive to a longitudinal firing motion to perform a surgical operation;
a shaft distally connected to the end effector;
a shaft firing member slidingly received by the shaft to transfer the firing motion to the end effector; and
a handle proximally connected to the shaft and firing member, comprising:
a flexible firing member having a distal end coupled to a proximal end of the shaft firing member,
a firing actuator reciprocally positioned by an operator to distally translate a distal portion of the flexible firing member,
a handle housing comprising a barrel portion positioned to guide the distal portion of the flexible firing member and comprising a stowage area communicating with the barrel portion and positioned to guide a deflected proximal portion of the flexible firing member during retraction; and
a drive chain mechanism operatively configured to couple the firing actuator to the flexible firing member;
wherein the flexible firing member comprises an articulated plurality of links attached to the drive chain mechanism.

16. The surgical instrument of claim 15, wherein the drive chain mechanism further comprises a one-way clutch engagement between the firing actuator and the articulated plurality of links for multiple firing strokes.

17. A surgical instrument, further comprising:
an end effector responsive to a longitudinal firing motion to perform a surgical operation;
a shaft distally connected to the end effector;
a shaft firing member slidingly received by the shaft to transfer the firing motion to the end effector; and
a handle proximally connected to the shaft and firing member, comprising:
a flexible firing member having a distal end coupled to a proximal end of the shaft firing member,
a firing actuator reciprocally positioned by an operator to distally translate a distal portion of the flexible firing member,
a handle housing comprising a barrel portion positioned to guide the distal portion of the flexible firing member and comprising a stowage area communicating with the barrel portion and positioned to guide a deflected proximal portion of the flexible firing member during retraction;
a drive chain mechanism operatively configured to couple the firing actuator to the flexible firing member; and
a retraction coil spring engaged between the handle housing and the drive chain mechanism for a retraction bias to the flexible firing member.

18. A surgical instrument, comprising:
an end effector responsive to a longitudinal firing motion to perform a surgical operation;
a shaft distally connected to the end effector;
a shaft firing member slidingly received by the shaft to transfer the firing motion to the end effector; and
a handle proximally connected to the shaft and firing member, comprising:
a flexible firing member having a distal end coupled to a proximal end of the shaft firing member,
a firing actuator reciprocally positioned by an operator to distally translate a distal portion of the flexible firing member,
a handle housing comprising a barrel portion positioned to guide the distal portion of the flexible firing member and comprising a stowage area communicating with the barrel portion and positioned to guide a deflected proximal portion of the flexible firing member during retraction;
a drive chain mechanism operatively configured to couple the firing actuator to the flexible firing member;
a longitudinal firing member guide comprising a cylindrical firing sleeve received for longitudinal rotation within the handle housing and including an inner diameter threaded longitudinal central bore, the flexible firing member comprising an outer diameter threaded flexible rod received in the central bore, an anti-rotation guide coupled between the handle housing and the flexible rod, and a firing transmission operatively configured to convert reciprocal motion of the firing actuator into a rotation of the cylindrical firing sleeve to effect distal translation of the flexible rod.

19. The surgical instrument of claim 18, further comprising a retraction mechanism operatively configured to store a counter rotation force during firing of the flexible rod.

20. A surgical instrument, comprising:
an implement portion responsive to a firing motion and diametrically dimensioned for endo-surgical use, the implement portion comprising:
a shaft;
a shaft firing member slidingly received by the shaft to transfer a firing motion;
an elongate channel coupled to the shaft;
an anvil pivotally coupled to the elongate channel, responsive to the closing motion from the shaft, and including an anvil channel;
a firing bar attached to the firing member and including a distally presented cutting edge longitudinally received between the elongate channel and the anvil; and
a staple device received in the elongate channel and responsively coupled to the firing bar to form staples against the anvil; and
a handle proximally connected to the shaft and firing member, comprising:
a longitudinal firing member guide aligned with a proximal portion of the shaft firing member;
a flexible firing member having a distal end coupled to a proximal end of the shaft firing member;
a firing actuator reciprocally positioned by an operator to distally translate a distal portion of the flexible firing member into the longitudinal firing member guide; and
a handle housing comprising a stowage area communicating with a proximal end of the longitudinal firing member guide to receive a deflected proximal portion of the flexible firing member during retraction;
wherein the longitudinal firing member guide comprises a cylindrical firing sleeve received for longitudinal rotation within the handle housing and including an inner diameter threaded longitudinal central bore, the flexible firing member comprising an outer diameter threaded flexible rod received in the central bore, an anti-rotation guide coupled between the handle housing and the flexible rod, and a firing transmission operatively configured to convert reciprocal motion of the firing actuator into a rotation of the cylindrical firing sleeve to effect distal translation of the flexible rod.

* * * * *